United States Patent [19]

Moskovich

[11] Patent Number: 5,496,320
[45] Date of Patent: Mar. 5, 1996

[54] MOSKOVICH CLAMPS FOR INTERLAMINAR CERVICAL FIXATION

[76] Inventor: Ronald Moskovich, 1010 Constable, Mamaroneck, N.Y. 10543

[21] Appl. No.: 195,478

[22] Filed: Feb. 14, 1994

[51] Int. Cl.$^6$ ..................................................... A61B 17/70
[52] U.S. Cl. ............................................... 606/61; 606/72
[58] Field of Search ......................... 606/61, 60, 53, 606/54, 72, 73, 74, 76, 86, 90, 102, 105; 602/6, 18, 900; 623/17, 901; 29/404; 364/413.01, 413.13, 468, 474.01, 476, 474.28, 474.29

[56] References Cited

U.S. PATENT DOCUMENTS

| | | | |
|---|---|---|---|
| D. 348,198 | 6/1994 | Crook | D8/73 |
| 1,390,732 | 9/1921 | Speicher . | |
| 1,789,740 | 1/1931 | Gelette . | |
| 2,631,346 | 3/1953 | Wengen et al. . | |
| 4,274,401 | 6/1981 | Miskew | 606/61 X |
| 4,611,582 | 9/1986 | Duff | 606/61 X |
| 4,648,388 | 3/1987 | Steffee . | |
| 4,846,431 | 7/1989 | Pflieger . | |
| 4,979,719 | 12/1990 | Sherman et al. . | |
| 5,074,864 | 12/1991 | Cozad et al. | 606/54 |
| 5,108,393 | 4/1992 | Ruffa . | |
| 5,267,999 | 12/1993 | Olerud | 606/61 |
| 5,352,225 | 10/1994 | Yuan et al. | 606/61 |
| 5,360,446 | 11/1994 | Kennedy | 623/16 |

OTHER PUBLICATIONS

Moskovich and Crockard, "Atlantoaxial Arthrodesis Using Interlaminar Clamps", *Spine*, vol. 17, No. 3, Mar. 1992, pp. 261–267.

*Primary Examiner*—Stephen C. Pellegrino
*Assistant Examiner*—Guy V. Tucker
*Attorney, Agent, or Firm*—Stephen C. Glazier

[57] ABSTRACT

The present invention provides a set of interlaminar clamps of specific and improved shapes to provide better fit to clamp together any two adjacent cervical laminae in the range from C1 to C7. These clamps are called Moskovich clamps, and their distinctive shapes are called Moskovich Curves. A method is also presented to manufacture similar cervical clamps for improved fit to clamp together any two adjacent cervical laminae throughout the entire back. This method is called the Moskovich Method. Morphometric data was taken for a large number of C1 through C7 laminae. Average shapes were then computed from this data for the C1 through C7 laminae. A small number of clamp shapes were then calculated that would fit these average cervical shapes. It was found that only a small number of clamp shapes were needed for clamps for the C1 through C7 range, and that these clamp shapes were different from what was available on the market in the prior art clamps. This method can be used to calculate average cervical shapes for all the cervical laminae of the back, and to make better fitting clamps for all the cervical laminae of the back. Also, the method can be used to calculate average body part shapes for any body part, and to make better fitting surgical implants to be attached to or placed in contact with that body part.

10 Claims, 19 Drawing Sheets

C2-7 TOP1

CLAMP 2

C2-7 TOP1

C2 LOWER

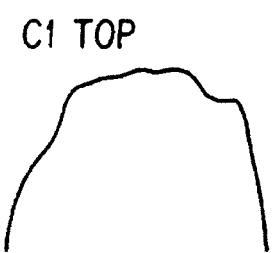
FIG. 12A
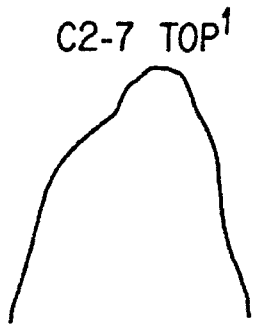
FIG. 12B
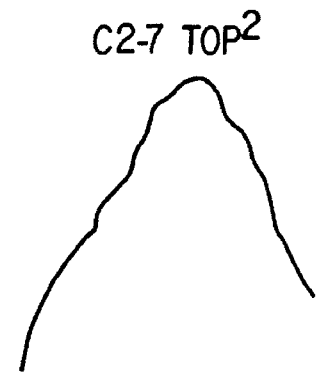
FIG. 12C
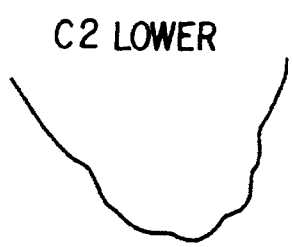
FIG. 12D
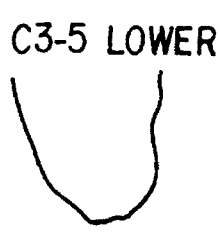
FIG. 12E
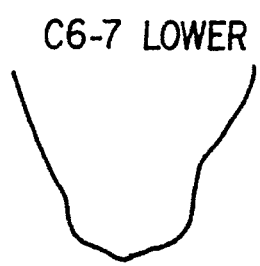
FIG. 12F
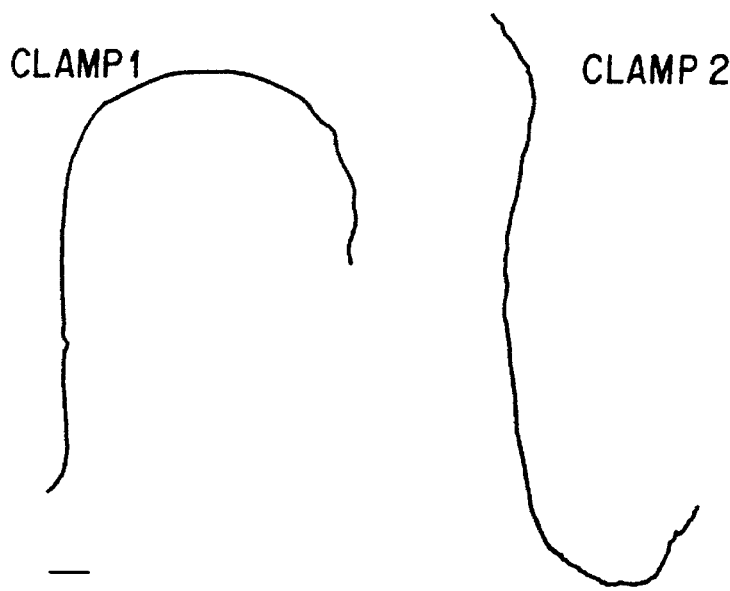
FIG. 12G
PRIOR ART
FIG. 12H
PRIOR ART

TOP OF C1

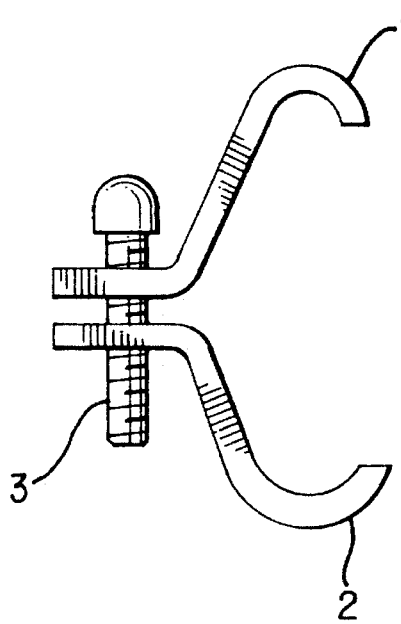
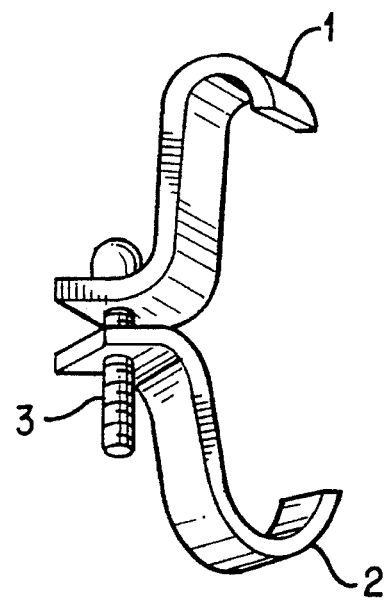
FIG. 19A
PRIOR ART
FIG. 19B
PRIOR ART
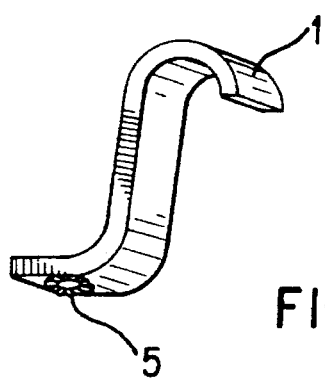
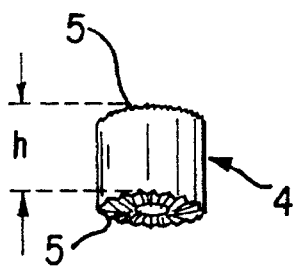
FIG. 20A
FIG. 20B
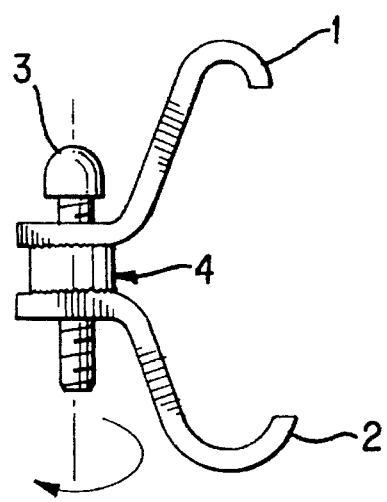
FIG. 21

MOSKOVICH CLAMPS FOR INTERLAMINAR CERVICAL FIXATION

1. FIELD OF THE INVENTION

This invention relates to the general field of orthopaedic surgical equipment, surgical implants and medical prostheses. More specifically, the invention relates to the field of clamps for the fixation of bones and bone grafts after surgery. Particularly, this invention relates to clamps for interlaminar cervical fixation after cervical surgery. The invention includes a new type of interlaminar cervical clamp, called here Moskovich clamps, and a method to manufacture such clamps.

2. BACKGROUND

A number of surgical techniques exist for posterior cervical arthrodesis. Onlay bone grafting and posterior wiring techniques (with or without bone blocks) are currently the most important surgical techniques in this area. These techniques have been supplemented recently by transfacet screw fixation and interlaminar clamp arthrodesis. The interlaminar clamp technique for posterior arthrodesis may prove to be superior to wiring techniques and simpler to perform than screw fixation methods, but the interlaminar clamp technique requires some improvement.

Interlaminar clamp fixation of the cervical spine has been in clinical use for approximately the past decade. Use of interlaminar clamp fixation has proven effective in achieving a satisfactory rate of posterior cervical fusion. There is, however, an incidence on non-union and loosening of the clamp fixation device.

The prior art interlaminar clamp is called a Halifax clamp, and is basically a variation of the common C clamp. FIGS. 19A and 19B show two views of a prior art Halifax clamp. The clamp has two opposing parts, each approximately in the shape of a "C", made out of bent pieces of flat metal bars. Additional representations of these opposing parts are provided in FIGS. 1, 2, 12G and 12H. The upper C-shaped part 1 and the lower C-shaped part 2 are fastened together at one end by a screw 3, which screw 3 is screwed to tighten the clamp. The current design of these prior art clamps is somewhat restricted in that there is a limited variety of clamp sizes and shapes available, which causes incidents of inaccurate fit of the clamps to the laminae. This poor fit problem may result in residual rotatory motion at the operated cervical segment, causing loosening of the clamp and possible disengagement of the clamp from the laminae.

The object of the present invention is to provide a set of new improved interlaminar cervical clamps that provide superior fit and hence do not loosen, and to provide a method to manufacture such clamps. Furthermore, it is an object of this invention to provide a general method of manufacturing better fitting surgical implants of all types.

3. SUMMARY

The present invention provides a set of interlaminar clamps of specific and improved shapes to provide better fit to clamp together any two adjacent cervical laminae in the range from C1 to C7. (C1 refers to the first cervical vertebra; C2 refers to the second cervical vertebra, and so forth to C7, which refers to the seventh cervical vertebra.) These clamps are called Moskovich clamps, and their distinctive shapes are called Moskovich Curves (sometimes referred to herein as M curves). A method is also presented to manufacture similar cervical clamps for improved fit to clamp together any two adjacent cervical laminae throughout the entire back. This method is called the Moskovich Method.

Morphometric data was taken for a large number of C1 through C7 laminae. Average shapes were then computed from this data for the C1 through C7 laminae. A small number of clamp shapes were then calculated that would fit these average cervical shapes. It was found that only a small number of clamp shapes were needed for clamps for the C1 through C7 range, and that these clamp shapes were different from what was available on the market in the prior art clamps. This method can be used to calculate average perimeter shapes for all the laminae of the back, and to make better fitting clamps for all the laminae of the back. Also, the method can be used to calculate average body part shapes for any body part, and to make better fitting surgical implants to be attached to or placed in contact with that body part.

4.1 BRIEF DESCRIPTION OF THE CHARTS

Chart 1 shows the X and Y Cartesian coordinates in millimeters of the C1 Top M Curve.

Chart 2 shows the X and Y Cartesian coordinates in millimeters of the C2 Bottom M Curve.

Chart 3 shows the X and Y Cartesian coordinates in millimeters of the C2-7 Top A M Curve.

Chart 4 shows the X and Y Cartesian coordinates in millimeters of the C2-7 Top B M Curve.

Chart 5 shows the X and Y Cartesian coordinates in millimeters of the C3-5 Bottom M Curve.

Chart 6 shows the X and Y Cartesian coordinates in millimeters of the C6-7 Bottom M Curve.

4.2 BRIEF DESCRIPTION OF THE DRAWINGS

Figure 1:
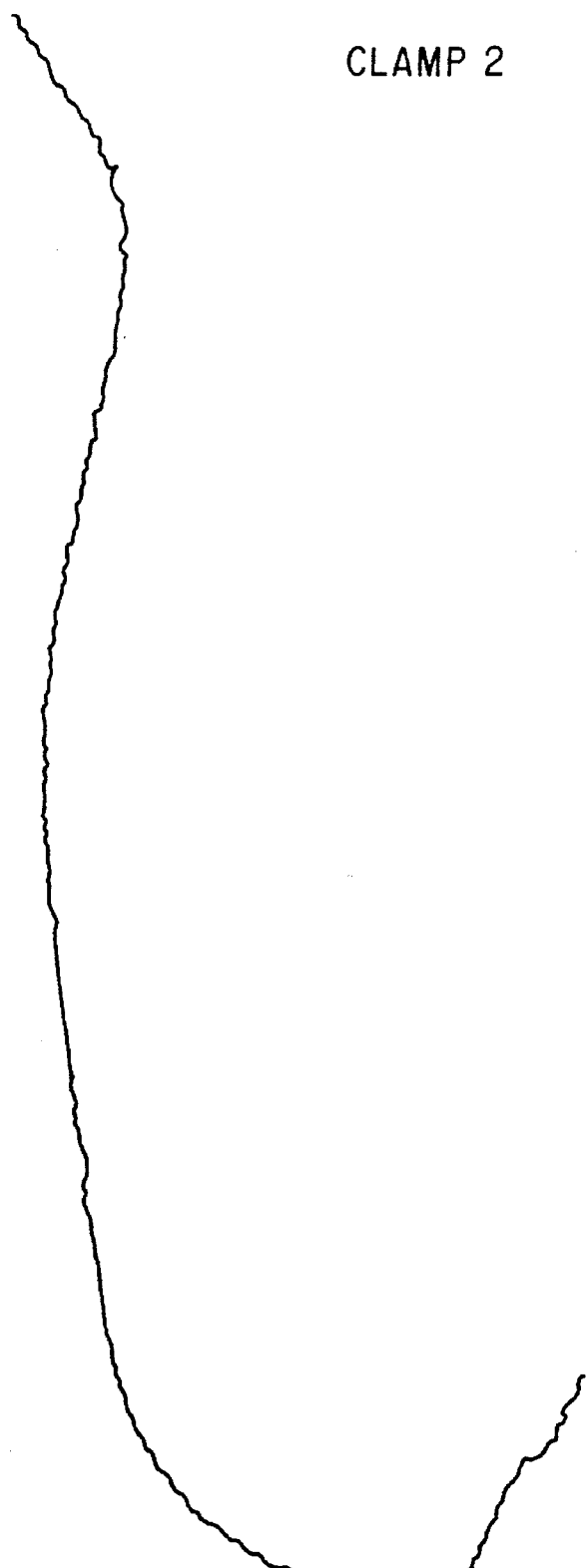
FIG. 1 shows the shape of the bottom of a prior art Halifax clamp.
Figure 2:
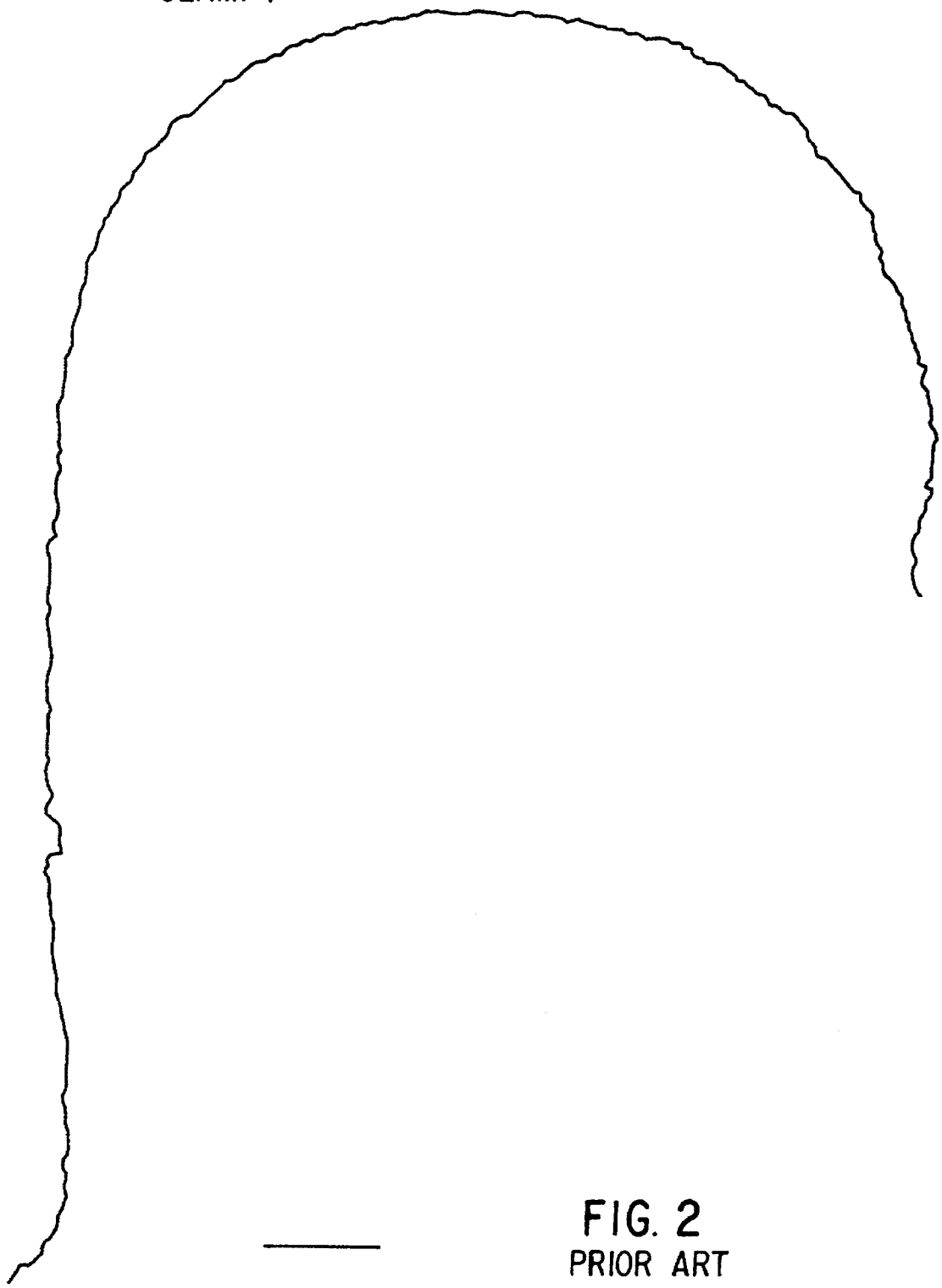
FIG. 2 shows the shape of the top of a prior art Halifax clamp.
Figure 3:
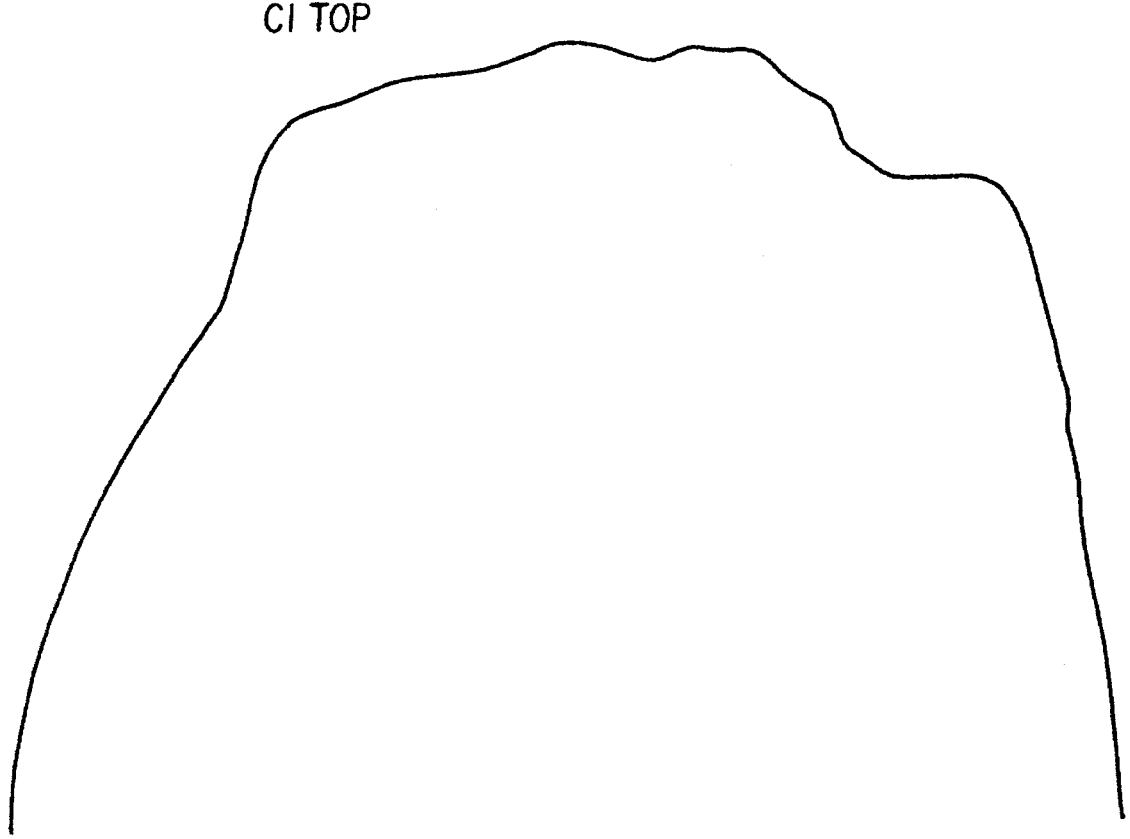
FIG. 3 shows the unsmoothed plot of the C1 Top M Curve.
Figure 4:
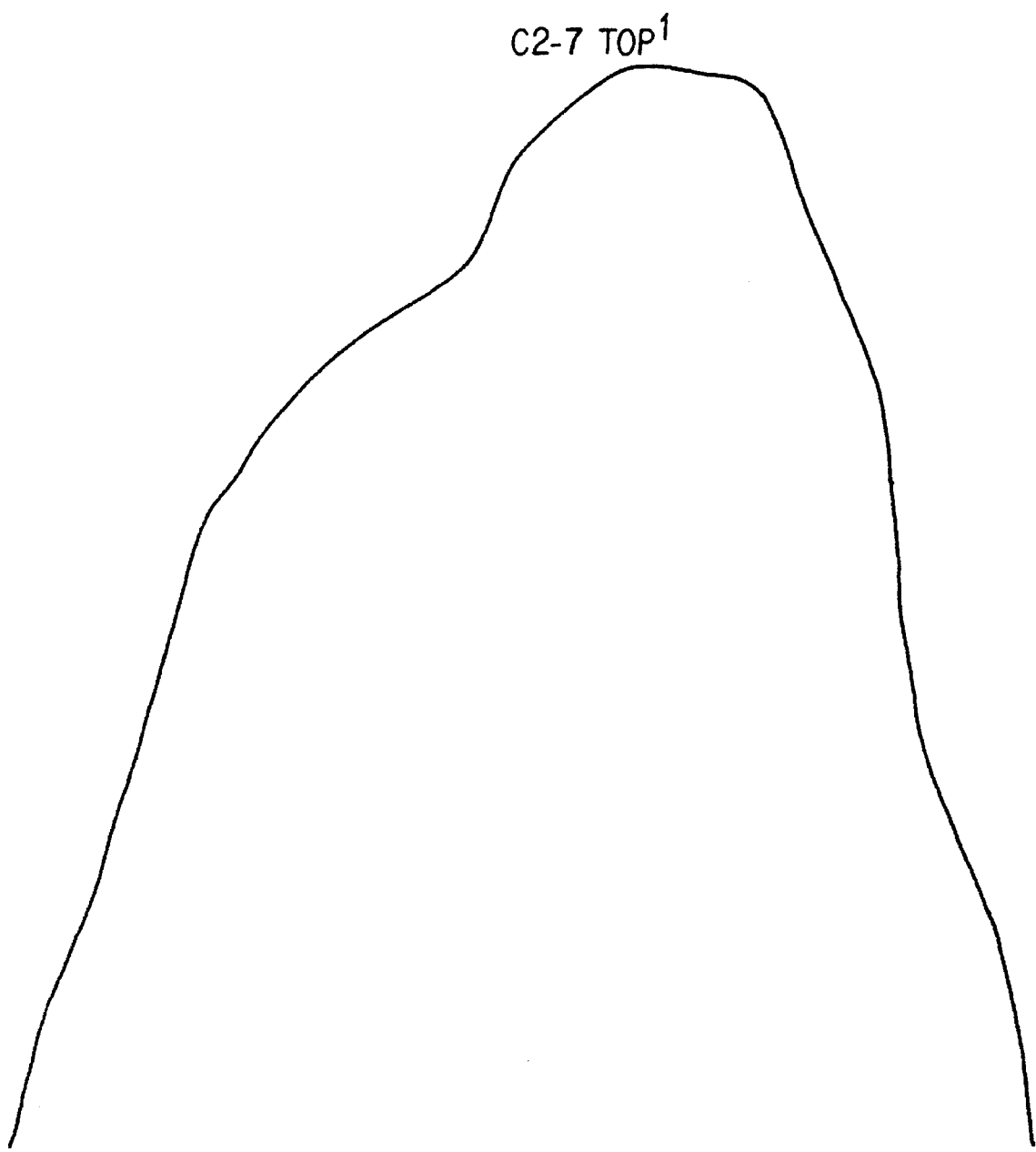
FIG. 4 shows the unsmoothed plot of the C2-7 Top A M Curve.
Figure 5:
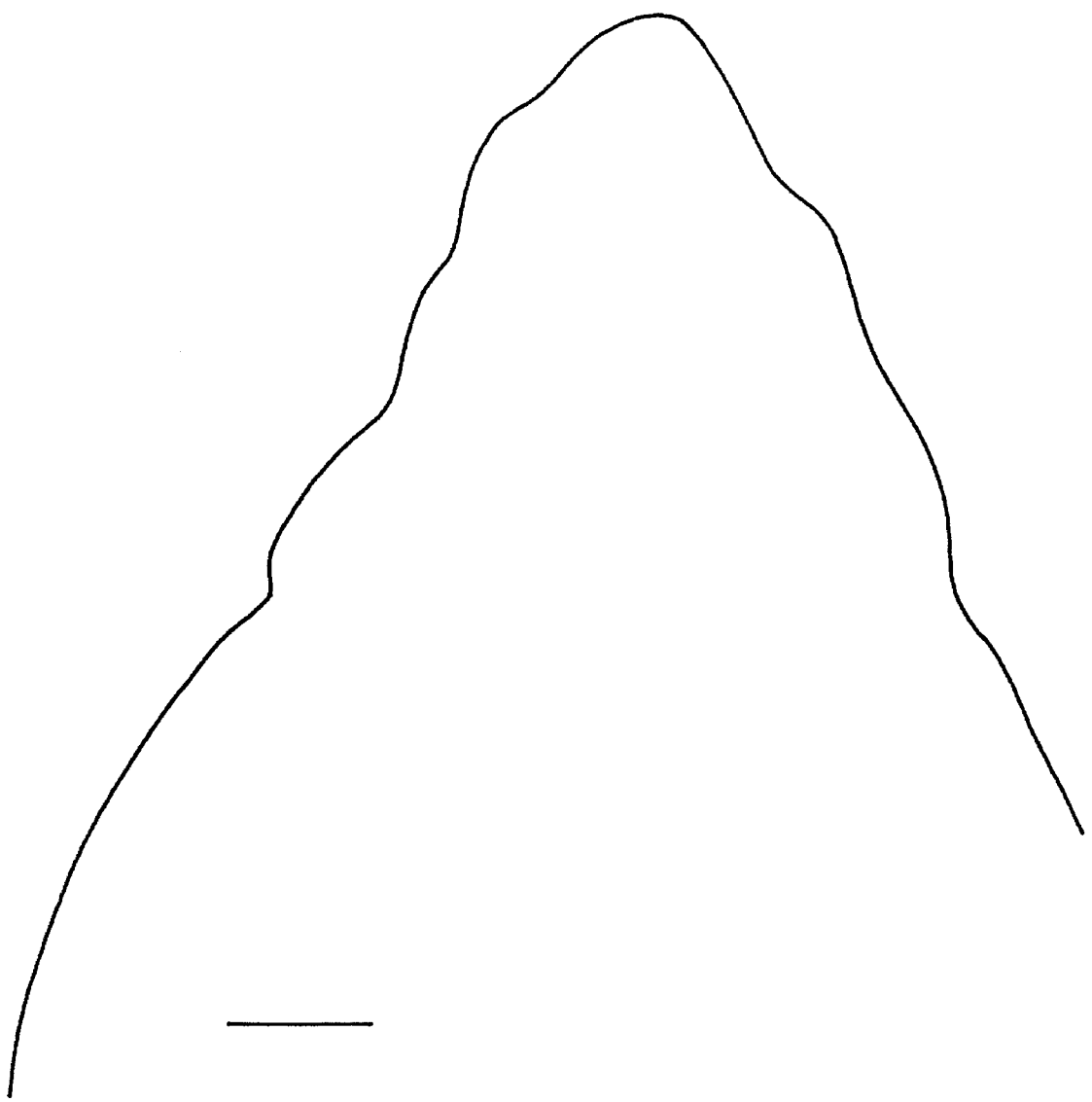
FIG. 5 shows the unsmoothed plot of the C2-7 Top B M Curve.
Figure 6:
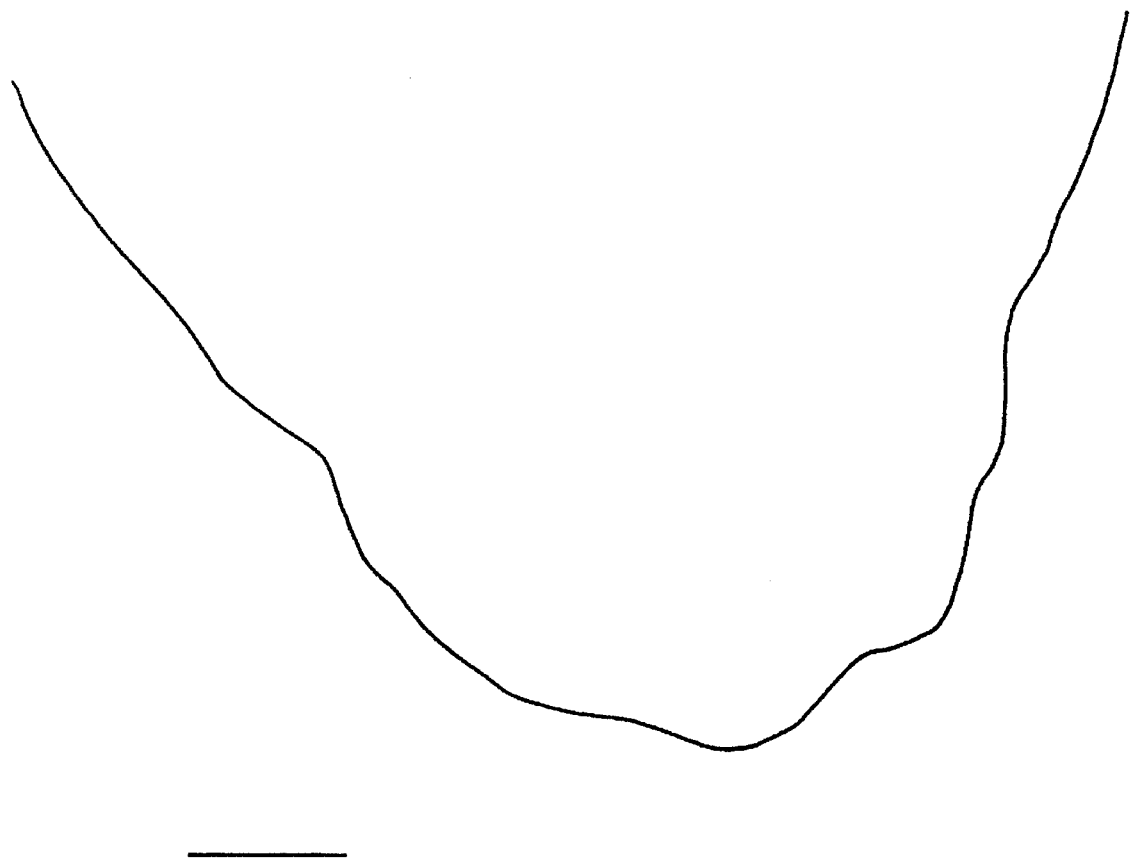
FIG. 6 shows the unsmoothed plot of the C2 Bottom M Curve.
Figure 7:
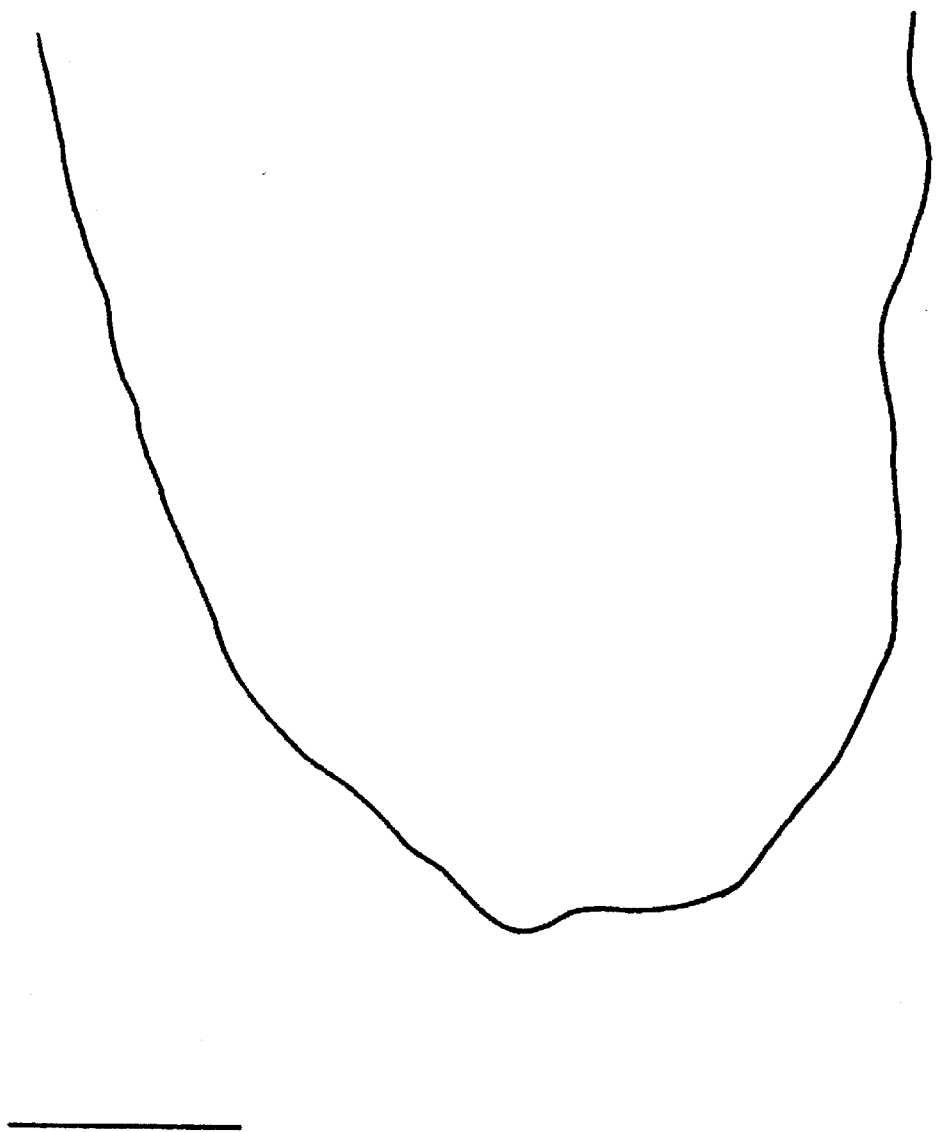
FIG. 7 shows the unsmoothed plot of the C3-5 Bottom M Curve.
Figure 8:
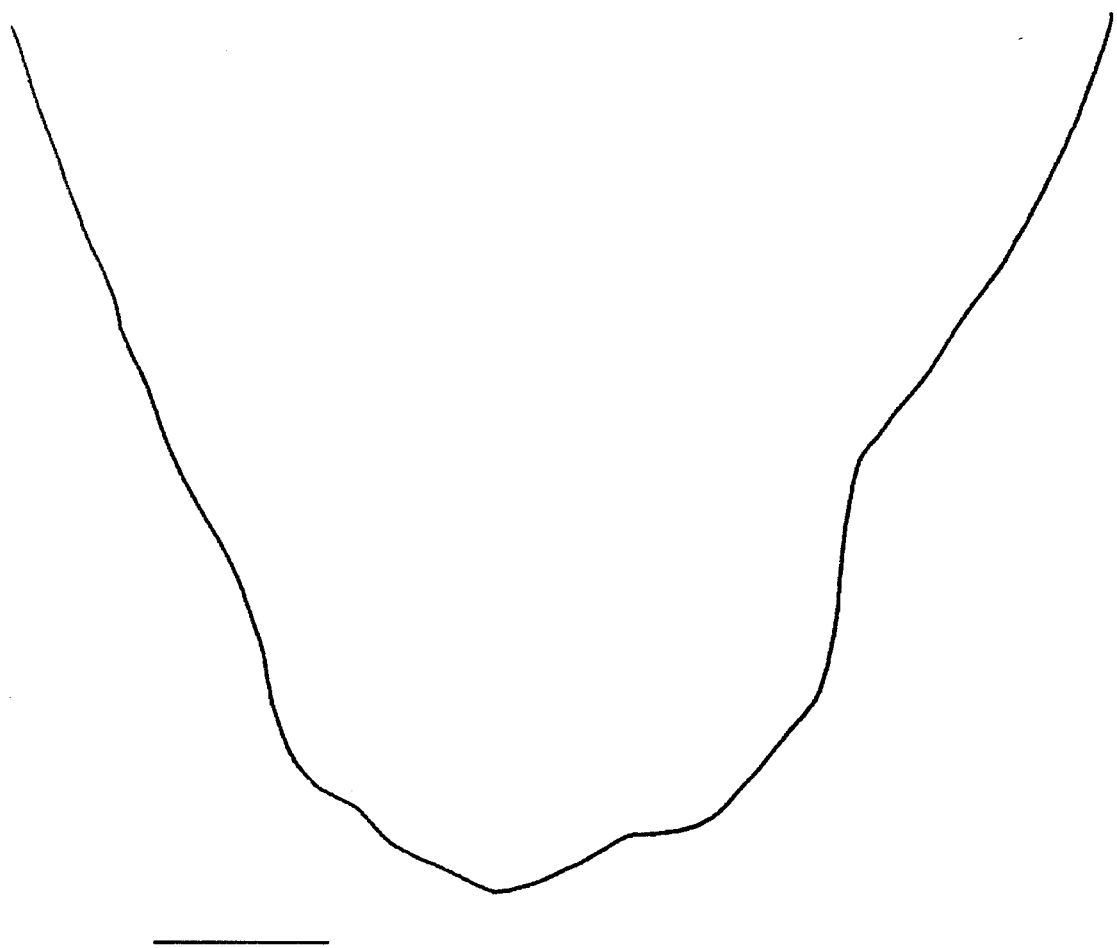
FIG. 8 shows the unsmoothed plot of the C6-7 Bottom M Curve.
Figure 9:
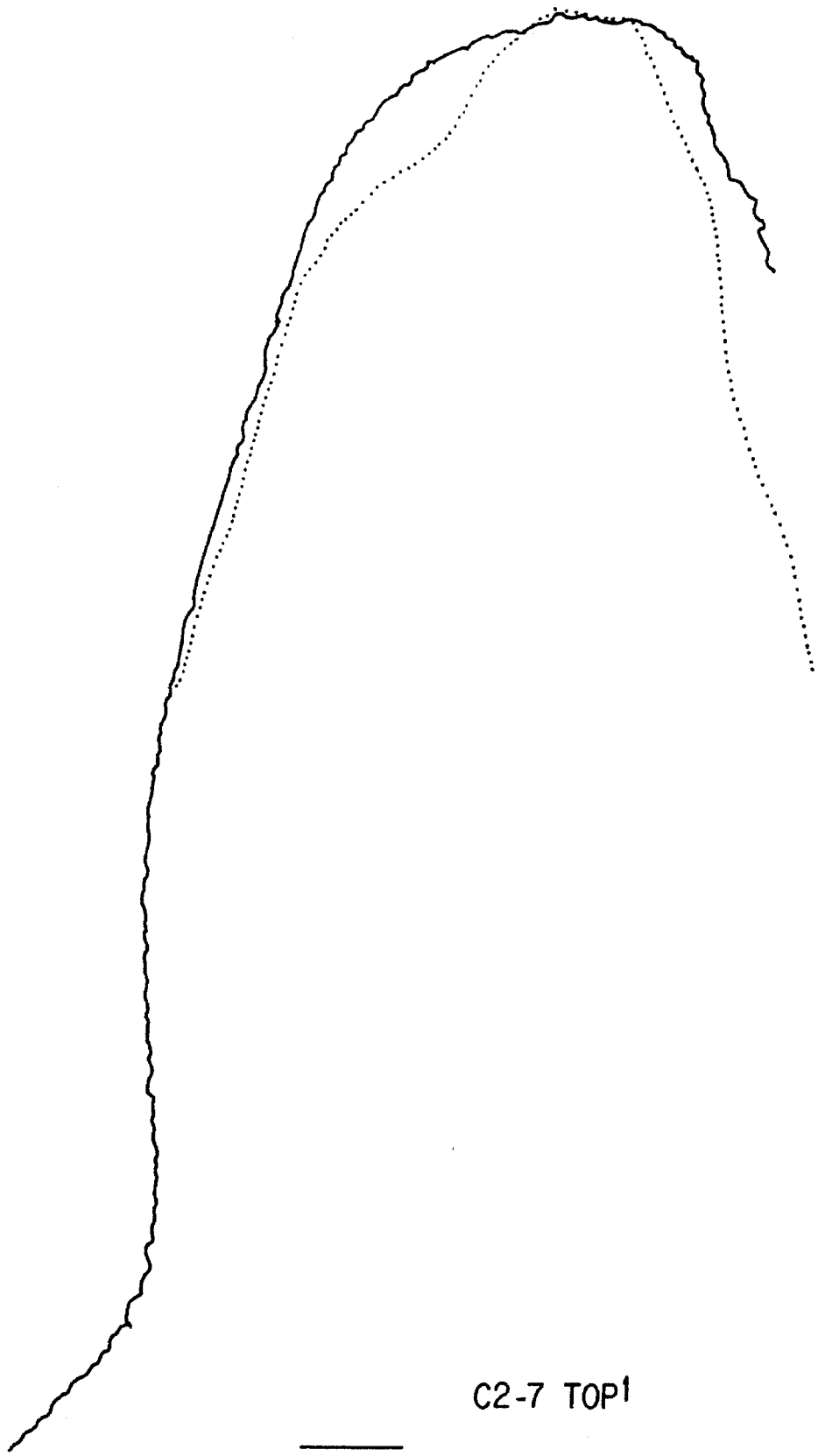

FIG. 9 compares the top of the prior art Halifax clamp and the C2-7 Top A M Curve, which is substantially different.

Figure 10B:
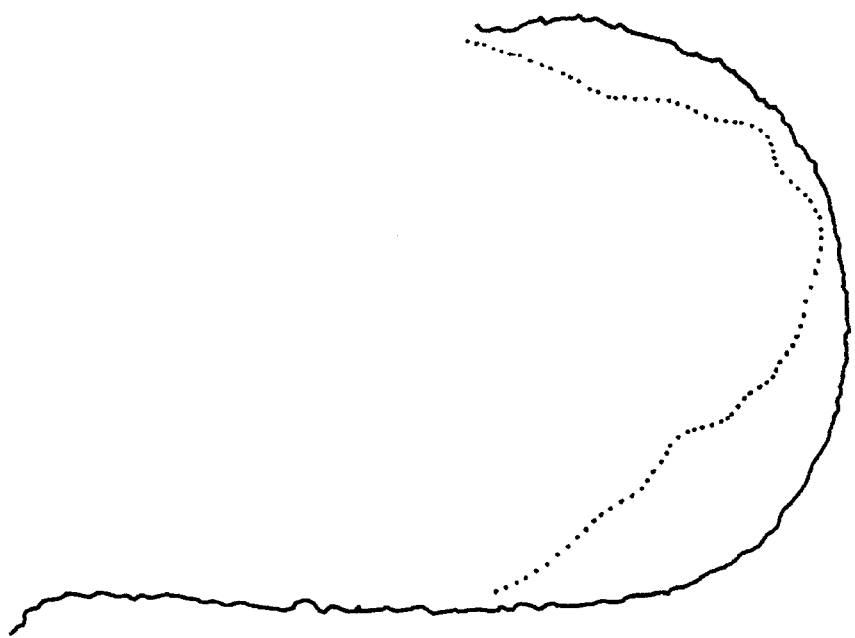
Figure 10A:
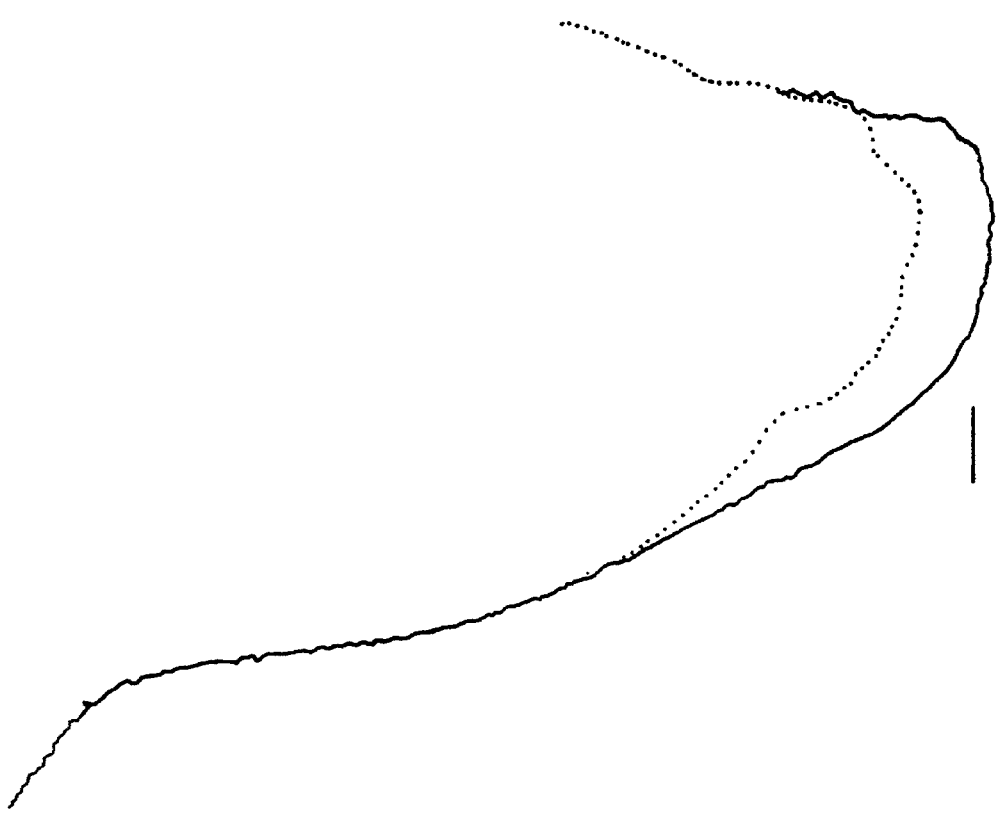

FIGS. 10A 10B compare two parts of the prior art Halifax clamp and the C2 Bottom M Curve, which is substantially different.

Figure 11B:
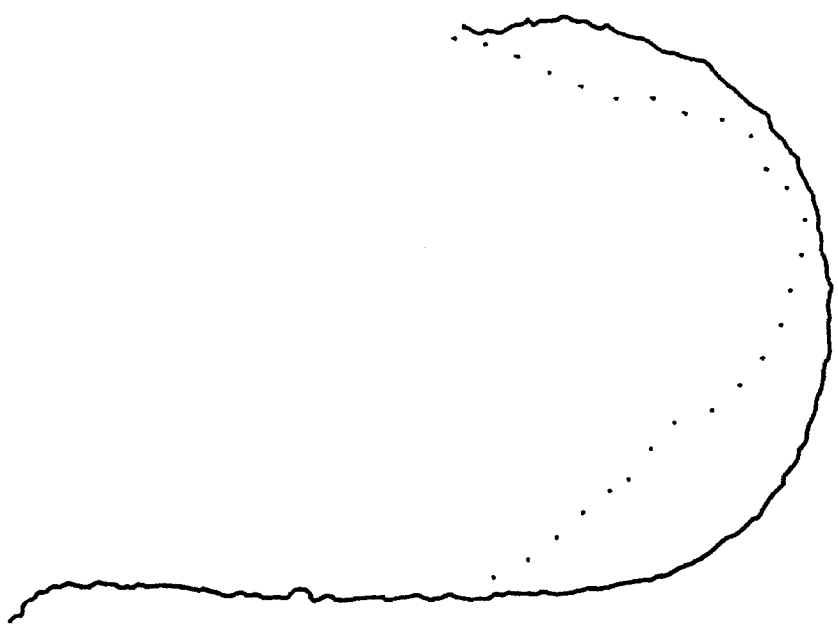
Figure 11A:
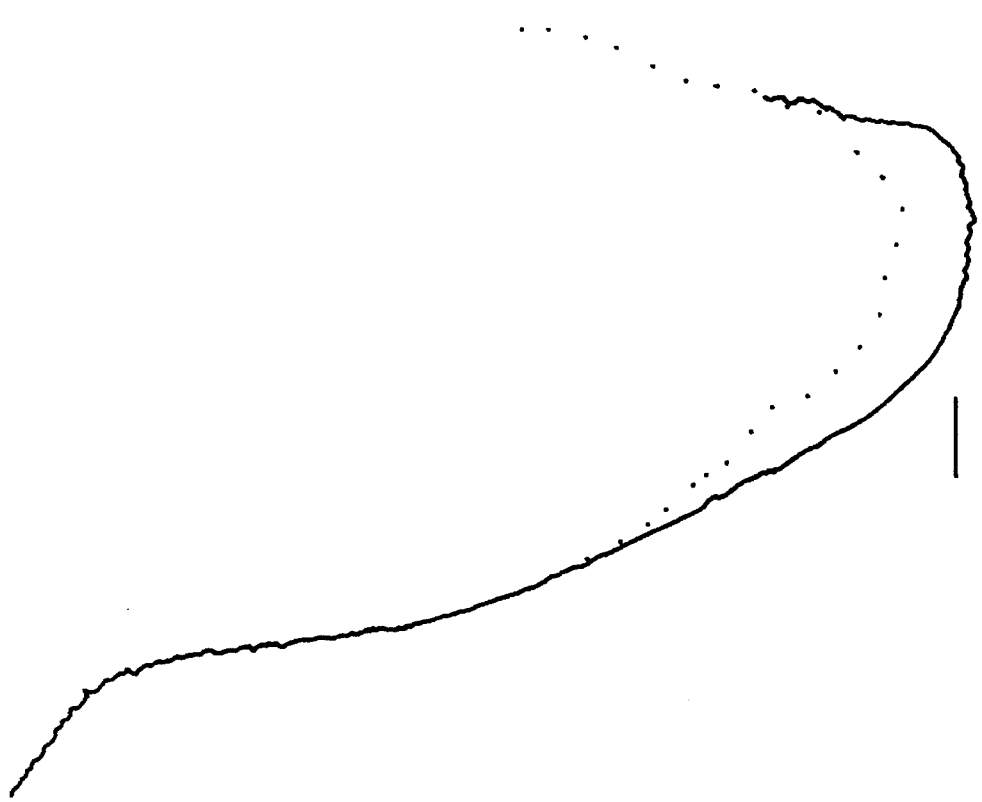

FIGS. 11A and 11B are the same as FIGS. 10A and 10B, except that the M Curve is more coarsely digitized.

FIG. 12A–12H it show and shows the information in FIGS. 1 through 8 together for ease of comparison.

Figure 13:
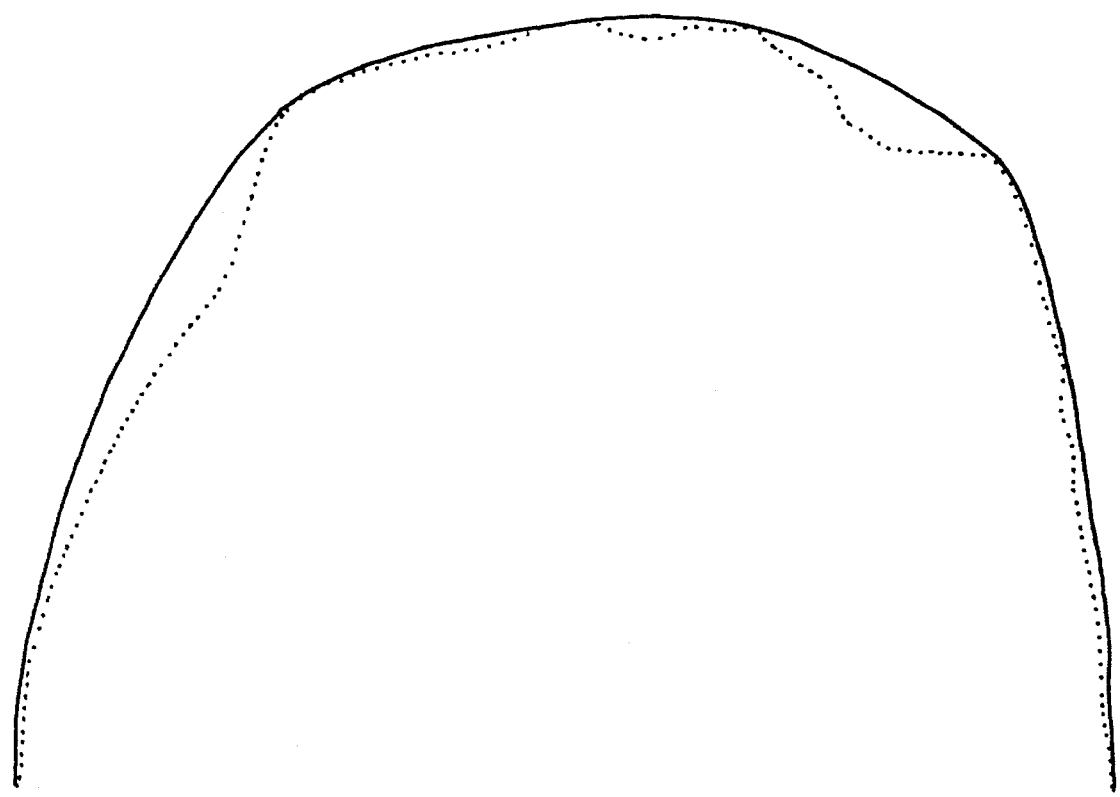

FIG. 13 shows the smoothed C1 Top M Curve.

Figure 14:
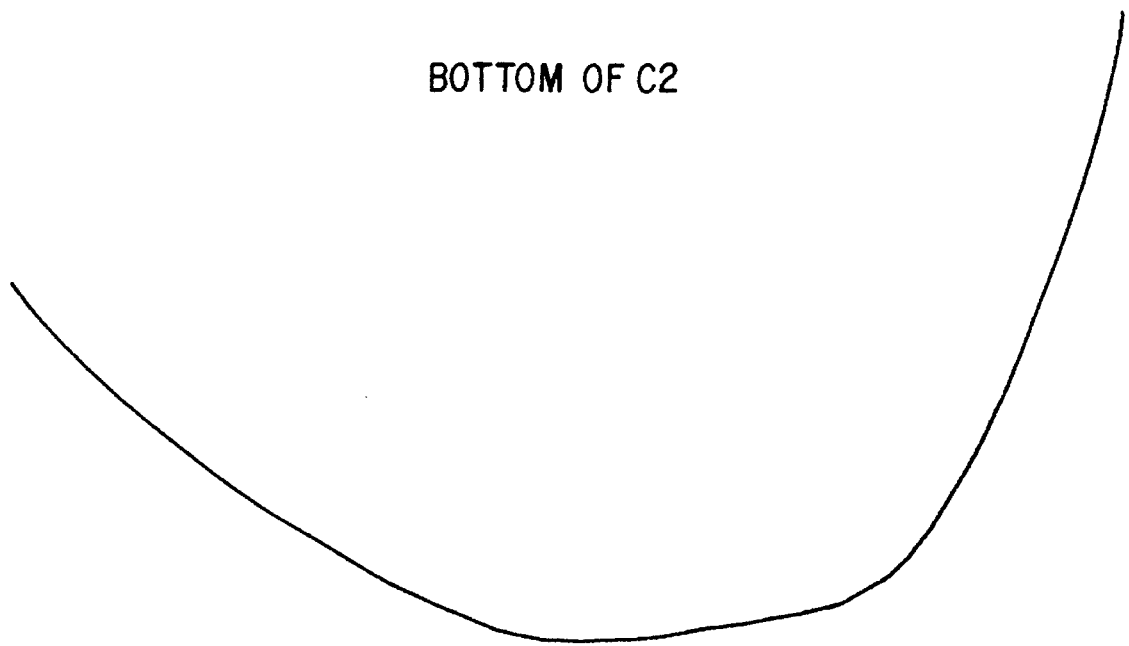

FIG. 14 shows the smoothed C2 Bottom M Curve.

Figure 15:
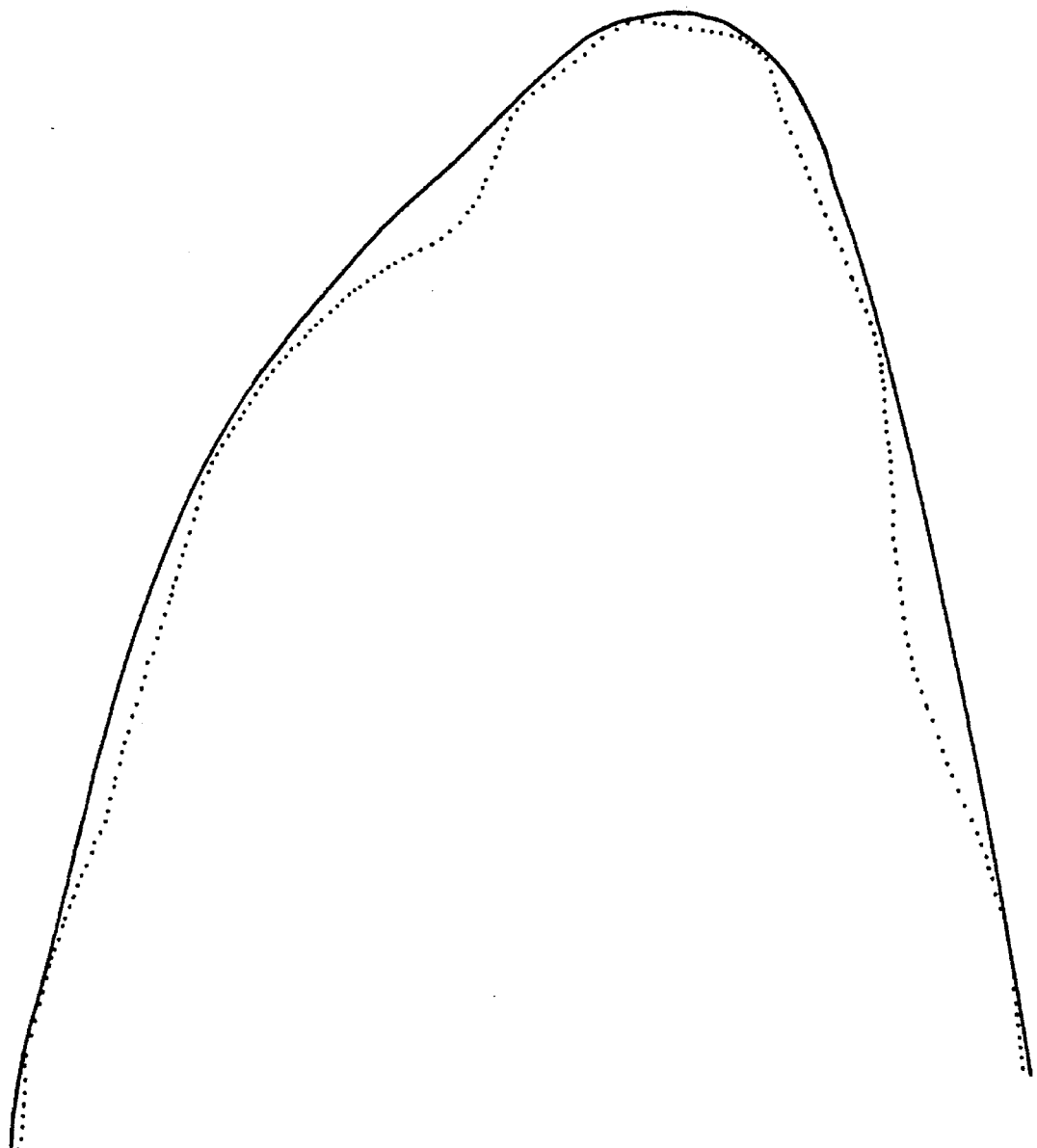

FIG. 15 shows the smoothed C2-7 Top A M Curve.

Figure 16:
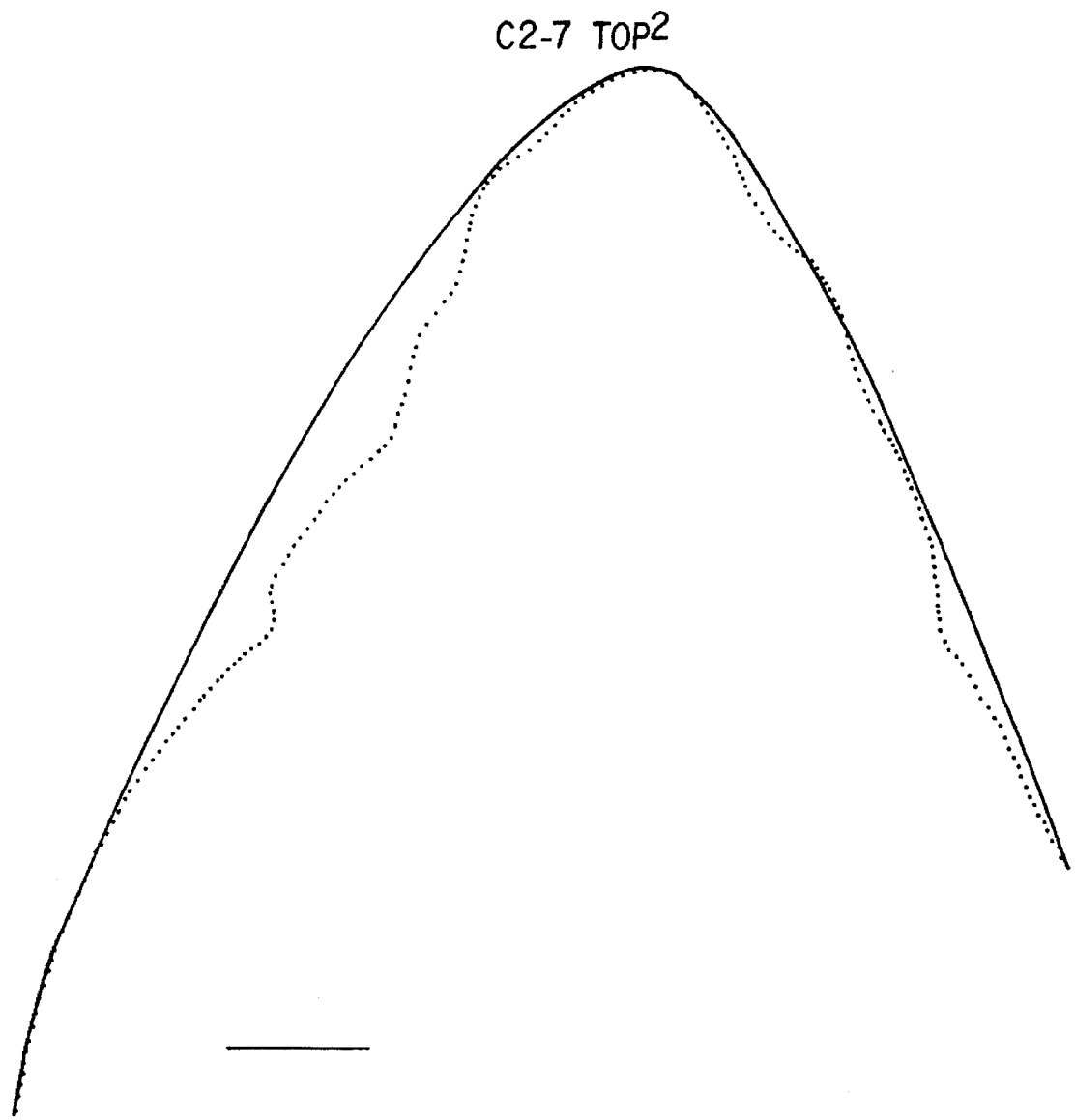

FIG. 16 shows the smoothed C2-7 Top B M Curve.

Figure 17:
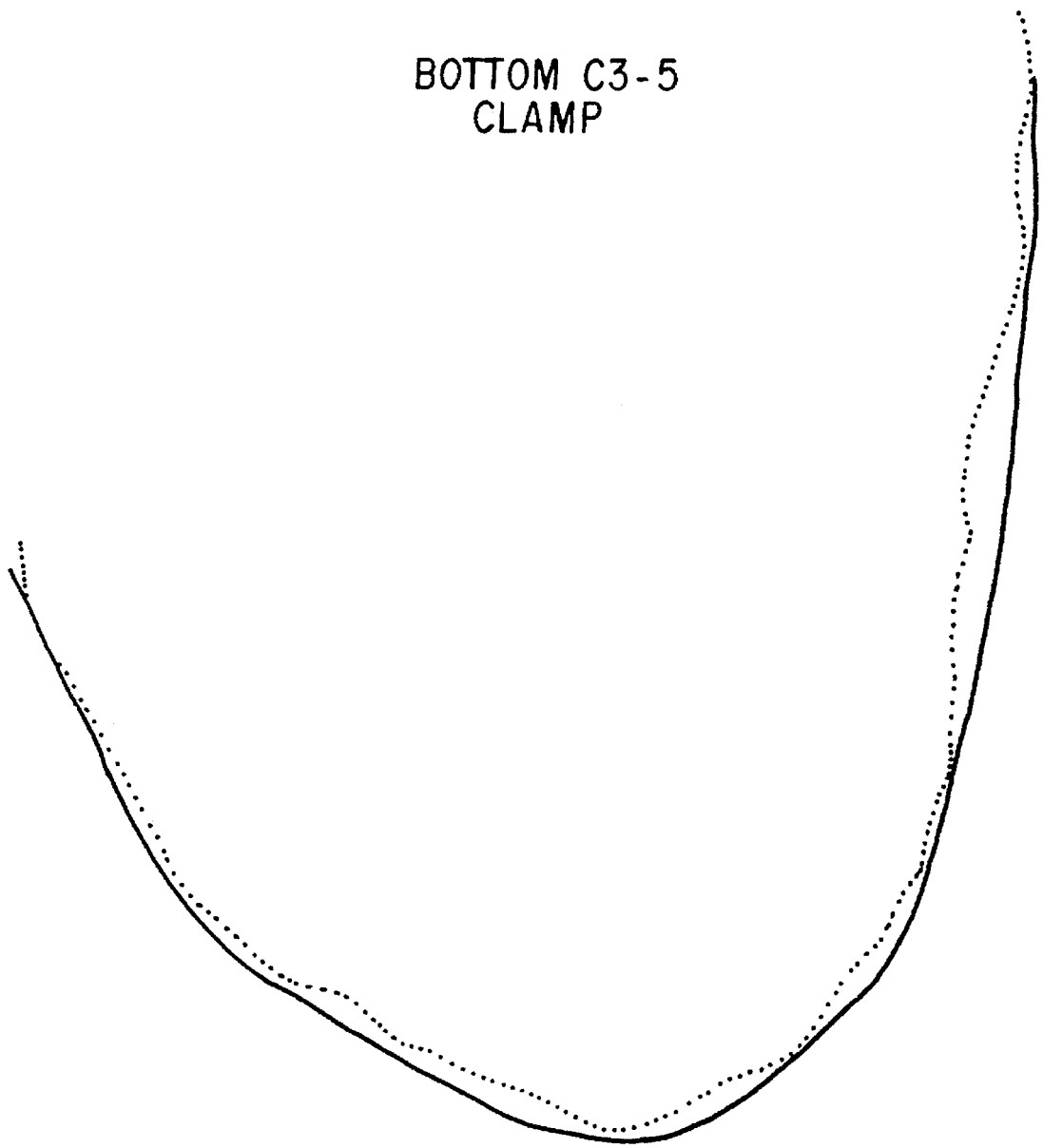

FIG. 17 shows the smoothed C3-5 Bottom M Curve.

Figure 18:
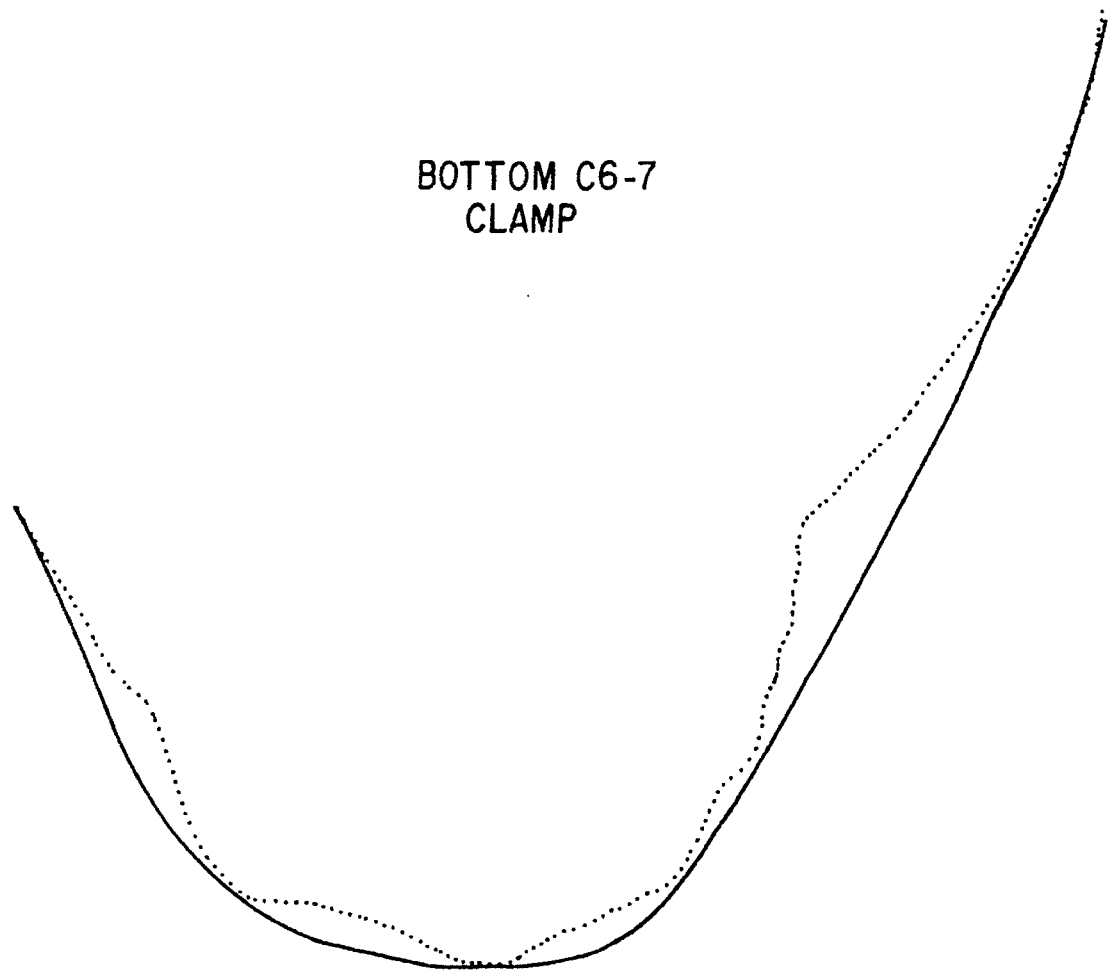

FIG. 18 shows the smoothed C6-7 Bottom M Curve.

FIGS. 19A and 19B shows two views of a prior art Halifax interlaminar cervical clamp.

FIGS. 20A and 20B show the radially grooved footplate of the Moskovich clamp, and the optional spacing sleeve in one of various heights "h" of the present invention.

FIG. 21 shows the spacing sleeve in position in the assembled interlaminar clamp of the present invention.

5. DETAILED DESCRIPTION OF THE PREFERRED EMBODIMENTS

The inventor undertook a study to provide morphometric data of the posterior elements of the cervical vertebra, in order to better appreciate the requirements for surgical implant clamp design in this area. Direct templating of human cervical laminae and computerized morphological analysis was undertaken to obtain this data. This method resulted in the design and construction of the first Moskovich clamps. The method is called the Moskovich Method and is applicable to make Moskovich clamps for all the laminae of the back.

5.1 Collect Specimen Vertebrae.

A collection of contemporary osteological specimens from the American Museum of Natural History in New York was used for the study. As indicated in Table 1 hereof, a total of 734 cervical vertebrae from 62 individuals were analyzed, representing specimens of vertebrae distributed from the C1 vertebra to the C7 vertebra. All the individuals except two were males. The age of the individuals at death ranged from 38 to 90, averaging 63 years old. The vertebrae were from one Eskimo, one Asian, nine Blacks and 51 Caucasians.

5.2 Measure the Shape of Each Specimen.

Direct measurement of lamina morphology was performed using a vernier caliper. Templates were then made of the middle part of each hemilamina using 1 mm diameter malleable wire (bilateral specimens were taken). Both ends of the wire were twisted together tightly, thus making a loop with a congruent fit to the lamina. A cut was then made in the loop so that the loop could be removed from the lamina without damaging the lamina. The loop was then repaired by laying the loop down on paper and fixing its position with scotch tape. The orientation of the loop, representing the circumferential or cross-sectional contour of the hemilamina, was carefully noted on the resulting wire-paper composite.

TABLE 1

| Vertebra | Number of Specimens |
| --- | --- |
| C1 | 102 |
| C2 | 108 |
| C3 | 108 |
| C4 | 110 |
| C5 | 110 |
| C6 | 100 |
| C7 | 96 |

5.3 Digitize and Store the Shape of Each Specimen.

The wire loops were photocopied and then optically scanned by an Epson ES-300C scanner at 300 dpi with 16 gray levels. The scanner was operated by the ScanDo software program on the Macintosh personal computer, which stored the images as TIFF files. The TIFF files were read in by the Adobe Photoshop program on the Macintosh, and the images were touched up using Photoshop. The touching up comprised attaching the breaks in the loops and thresholding at a 50% gray level. The improved images were uploaded to a mainframe computer.

On the mainframe computer, a boundary-following algorithm traced the inner edge of each loop. The curve generated thereby matched the curve of the inner edge of each loop, which in turn matched the curve of the outer surface of the laminae to which the loop was attached. This curve generated in the mainframe was represented by points in the loop bordering on the hole inside the loop, not points in the hole bordering on the loop. The edge of the curve was one pixel thick and had diagonal jumps across concave turns. The edge was represented as a list of X and Y coordinates for successive pixels, going counterclockwise.

Major and minor axes were defined and computed for the curves based on the following. It can be shown that if M is $$\begin{bmatrix} \sigma_{xx} & \sigma_{xy} \\ \sigma_{xy} & \sigma_{yy} \end{bmatrix},$$

the covariance matrix of the x and y values of the points in the figure, then the eigenvector of M corresponding to the larger eigenvalue is the direction of the greatest scattering, that is, the direction in which the points have the greatest variance. Hence, the eigenvector corresponding to the smallest eigenvalue is the direction of least scattering, that is, the direction in which the points have the least variance. Since the covariance matrix is symmetric, these two vectors must be orthogonal, and therefore it is reasonable that the major and minor axes should lie in the directions of the former and latter vectors respectively.

When the covariance matrix is computed for the x and y values, as described, one may use the x and y values of the vertices of the boundary, the x and y values of the entire boundary (using line integrals), or the x and y values of the entire figure (using integrals over the figure). In the last case, integrals over the figure can be replaced by line integrals by means of Green's theorem. The variances of x and y over the N vertices, which are used in the first method, are represented as follows:

$$\sigma_{xx} = \sum_{1}^{n} (X_i - \bar{X})^2, \sigma_{yy} = \sum_{1}^{n} (Y_i - \bar{Y})^2 \sigma_{xy} = \sum_{1}^{n} (X_i - \bar{X})(Y_i - \bar{Y})$$

In the last two methods, the line integrals can be computed exactly since the boundary consists of line segments and the integrand is always $X^n Y^m$ for some $n, m \geq 0$. The loop is parameterized by $x(t), y(t)$, $t = [0,1]$, in the second and third methods of calculation. In the second method, $\sigma_{xx}$=Arc length integral of $(x(t) - \bar{X})^2$ over the loop; $\sigma_{yy}$ is similar, and; $\sigma_{xy}$ =Arc length integral of $(x(t) - \bar{X})^2 (Y(t) - \bar{Y})$ over the loop. The third method calculates $\sigma_{xx}$ as the integral of $(x - \bar{X})^2$ over the region enclosed by the loop, and calculates $\sigma_{yy}$ and $\sigma_{xy}$ similarly.

The disadvantages of the first method is that it requires that the vertices be distributed rather evenly along the boundary in order that they be representative of the figure as a whole, and it is easy to construct a figure and a corresponding list of vertices for which the algorithm does poorly. However, in the case of the present preferred embodiment, the points were always very evenly distributed, and this algorithm requires the least computation of the three. The second algorithm requires the most computation because it needs to compute a square root for each line segment in the boundary in order to calculate the segment's length. However, in the case of the present preferred embodiment, every segment is exactly one unit long or exactly two units long, and the square root of two can be stored in advance. The third algorithm requires that the curve not cross itself (although intersection without crossing is allowable). In the present preferred embodiment, none of the curves cross themselves. Note that the three methods generally produce slightly different sets of eigenvectors. The first method was used in the present invention in the preferred embodiment.

There are other possible definitions for the major and minor axes, some more reasonable than others. The diameter of the figure, i.e., the longest segment whose endpoints lie on the boundary of the figure, could be called the major axis. There may be an algorithm of order n, where n is the number of vertices needed to compute this major axis. However, this definition is unsuitable, because if the figure is a rectangle, then the major axis would be a diagonal of the rectangle according to this definition, it is intuitively necessary for the major axis to run parallel to the longer sides of the rectangle. One could define the minor axis as a segment parallel to the direction along which the figure is shortest, i.e., the direction for which the width of the projection of the figure onto a line in that direction is minimized. There may be an algorithm of order n for this as well. However, this definition is also unsuitable, because in the case of a rhombus it would mean that the minor axis is parallel to one of the altitudes of the rhombus, whereas it is intuitively required that the minor axis be the shorter crossbar of the figure.

one could also define the length and width of the figure in a particular direction, the length being the length of the projection of the figure onto a line in that direction, and the width being the length of the projection onto a line perpendicular to the first, and then define the major axis as a segment parallel to the direction for which length/width is maximized. There should be an order-n algorithm for this as well.

An effort was made to determine the angle at which the bone actually lies in the spine of a person standing erect, that is, the angle that the major axis makes with the vertical. This could not be done with great accuracy and it was later decided that it was unnecessary. Instead, it is merely necessary to know which end of the loop is higher, that is, which end of the loop would lie above the other if it were wrapped around the bone while the bone was still in the person and the person was standing erect. The other end of the loop is said to be lower.

5.4 Extract the Top and Bottom Parts from Each Specimen Shape.

The "top" and "bottom" parts (called herein "fishheads", after their general shapes) of each loop were extracted as follows. The loop was rotated so that its major axis was vertical and the higher end of the loop was lying on the positive x-axis, the second sector lying in the first quadrant adjacent to the first sector, and so on. Each vertex in the fishhead was identified by its polar coordinates, ρ and θ, and the initial assumption was made that for any $0 \leq \psi 23\ 2\pi$, there is no more than one point in the fishhead whose θ equals ψ, and therefore ρ can be considered a function of θ. An average value of ρ was determined for each sector by integrating $\rho^2$ with respect to θ for all θ in the sector, dividing by the width of the sector (6 degrees), and taking the square root. If a "spoke" were drawn from the central point to the fishhead along the bisector of the sector, then the result of this computation can be thought of as the length of the spoke.

The importance of choosing a fishhead's central point correctly is illustrated by the following scenario. Suppose two fishheads have the shape of an upper semicircle of unit radius. Since they are identical, their descriptions in terms of spoke lengths should be identical as well. Suppose, however, that one fishhead's central point was chosen at the bottom left, near the left tip of the fishhead, and the other fishhead's central point was chosen high on the fishhead's axis of symmetry. This would result in great differences in length between corresponding spokes of the two fishheads.

It is therefore necessary to choose a fishhead's central point in such a way that if one fishhead is translated with respect to another in such a way that the central points of the two fishheads coincide, then the fishheads will be aligned as closely as possible. Of course, it is necessary to state precisely what is meant by close alignment. One approach is as follows. Suppose the two curves are defined by $(x_i, y_i)$ i=1. . . M, and $(x'_j, y'_j)$ j=1. . . N. Define a $D_1$ distance by $$D_1 = \sum_{i=1, j=1}^{i=N, j=N} (x_i - x_j')^2 + (y_i - y_j')^2.$$

This distance is minimized when the centroids of each set of vertices coincide, and if we normalize the distance by dividing by NM, the minimized distance equals $\sigma_{M,N} \delta(x) + \sigma_{M,N}\delta(y)$ where $\delta_i(x)=x_i-x', \delta_i(y)=y_i-y'_i$, and where $\sigma_{M,N}$ denotes variance over all MN values.

Another approach is as follows. Suppose that the curves are described by the vertex sequences $(x_i, y_i)$ i=1. . . N, and $(x'_i, y'_i)$ i=1. . . N, that is, the two curves have the same number of vertices. Suppose also that in each curve, adjacent pairs of points are equally spaced in terms of arc length. Then define the distance between the curves as $$D_2 = \sum_{i=1}^{n} (x_i - x_i')^2 + (y_i - y_i')^2.$$

It is easily shown that this distance is minimized when the curves are translated with respect to each other in such a way that the centroids of each set of vertices coincide. Also, if the distance is normalized by dividing N, it can be shown that this minimized distance equals $\sigma_N(x)=\sigma_N\delta(y)$, with $\delta_i(x)$ and $\delta_i(y)$ defined as before, and where $\sigma_N$ denotes the variance over all N values. The assumption that adjacent pairs of points are equally spaced is only approximately true with the fishheads, and the assumption that two curves have the same number of points is, in general, not true at all. Nevertheless, the fact that both of these types of distances are minimized when the centroids of the sets of vertices coincide suggests that two fishheads should be considered optimally aligned when the centroid of the vertices of one fishhead coincides with the centroid of the vertices of the other. It follows that the central point of a fishhead should be either the centroid of the vertices or a point at a fixed displacement from the centroid.

For the bottom fishheads, a point 8 units above the centroid was used. For top fishheads, a point 7.5 units to the right of the centroid was used. (Here, a unit equals 1/300th of an inch.) The shifting ensured that the central point always lay inside the fishhead and reduced the number of fishheads in which cropping of the curve was needed in order to make r(θ) single-valued.

If there were values of θ in the sector with no corresponding points in the fishhead, then instead of dividing by the width of the sector, the computer program divided by the measure (size) of the part of the sector for which there were points in the fishhead. If no points in the fishhead corresponded to any of the values of θ in the sector, then no spoke was "drawn" for that sector; i.e., no spoke length was computed. If the fishhead "doubled back" in the sector, and consequently there were values of theta in the sector for which there was more than one point in the fishhead, then instead of integrating $\rho^2$ over the sector, the computer program integrated $\rho_{max}2$, where $\rho_{max}\theta$ is the maximum of $\rho$ taken over all the points in the fishhead at angle $\theta$. The rationale for using the maximum was that a clamp fitting around the outside of the fishhead presumably would have rested on the part of the fishhead farthest from the centroid.

The reason the square root of the average $\rho^2$ was used, rather than simply taking the average of $\rho$, is that before the reparameterization, the fishheads were all represented as sequences of vertices, which is equivalent to representing them as chains of line segments. And whereas it is computationally expensive to integrate r along a line segment analytically, the integral of $\rho^2(\theta)$ d$\theta$ along a line segment from (x1,y1) to (x2,y2) can be shown to equal the absolute value of the cross product of (x1,y1) and (x2,y2).

Actually, the integral of $\rho\theta$ can be computed analytically as follows. If a line is drawn from the origin perpendicular to the segment (x1, y1)—(x2,y2), then the integral in question is $$D \int_{\theta_1}^{\theta_2} \sec\theta d\theta,$$

where D is the distance (along the perpendicular line) of the segment from the origin, and $\theta_{13}i$ is the angle that the vector (xi,yi) makes with the perpendicular line. The indefinite integral of sec $\theta$ is |N |sec $\theta$+tan $\theta$|. Everything besides the log can be computed from x1, x2, y1, y2 using arithmetic operations and three square roots.

The new parameterization in effect standardized the fishheads, because the same set of sectors were used for every fishhead, and this standardization facilitated computation of clamp shapes. Like the re-parameterized fishheads, a clamp was described (in fact, defined) by specifying its distance from a reference point in each of the sectors. Then, a clamp was said to fit an upper fishhead if all of the following conditions were satisfied:

a) None of the spokes of the fishhead were more than 0.197 millimeters longer than the corresponding spoke of the clamp (i.e., spoke of the clamp in the same sector).
 b) There was no sector in which the fishhead spoke was more than 0.039 millimeters shorter than the clamp spoke. (The fishhead spoke was allowed to be slightly shorter because the bone was slightly compressible). In sectors in which either the clamp or the fishhead had no spoke, this condition was not applicable.
 c) In at least four of the sectors which were at least partially in the upper half-plane, the fishhead spoke was no more than 0,130 millimeters longer than the clamp spoke.

The conditions to be satisfied in order for a clamp to fit a bottom fishhead were the same, except that in condition (c) one looked at the sectors which were at least partially in the lower half-plane.

5.5 Partition the Specimen Shapes into Clusters and Compute a Clamp Shape to Fit Each Cluster. A computer program was then written that took all the fishheads in a given subset and partitioned them into clusters in such a way that all the fishheads in a cluster could be fitted by a single clamp. The algorithm used was similar to an agglomerative clustering algorithm, except that where the latter tries to form clusters which are as "tightly packed" as possible, the algorithm used here did not attempt to make a cluster any "tighter" than necessary to fit all the fishheads in it with a single clamp. The program then outputted the descriptions of the clamp shape that fit each cluster. These clamp shapes and curves are shown in Figures 3 through 8 and 12A through 12F, and Charts 1 through 6, herein. A comparison of certain ones of these shapes and curves with corresponding shapes and curves of a prior art Halifax clamp is made in each of FIGS. 9, 10A, 10B, 11A and 11B.

In this way, a single clamp shape was computed to fit the top of every C1 specimen (the C1 Top M Curve), and a pair of clamp shapes was computed such that the top of every specimen of C2 through C7 was fitted by one of the two shapes (the C2-7 Top A M Curve and the C2-7 Top B M Curve). (Although it was not intended to fit clamps to the top of C7 laminae, it was found that including the C7 top fishheads in the subset partitioned by the clustering algorithm did not increase the number of clamps necessary.) For the bottom fishheads, one clamp shape was computed that fit all C2 specimens (the C2 Bottom M Curve), one clamp shape was computed that fit all specimens of C3 through C5 (the C3-5 Bottom M Curve), and one clamp shape was computed that fit all specimens of C6 and C7 (the C6-7 Bottom M Curve). A second program verified that each clamp actually fit every fishhead that the first program claimed the clamp fit.

5.6 Smoothing the Clamp Shapes.

Contrary to intuition, some of the computed clamp shapes had sharp inward bends which were apparently caused by the existence of a few fishheads with very marked inward bends in the same position. It was found that these inward bends could be smoothed without causing the clamp not to fit any of the fishheads it had fit previously. This smoothing was done by computer using Bezier curves to form the plots of the clamp shapes. These smoothed clamp shapes are shown in FIGS. 13 through 18, herein.

As explained above, each clamp shape was defined by its spokes, i.e., by its distance from a reference point at each of a sequence of angles increasing by increments of six degrees. This, in effect, provided a sequence of vertices in the clamp shape, and the shape could be depicted by drawing the polygonal line connecting the vertices. Instead of using this jagged depiction of the shape, an additional program was used to interpolate a twice continuously differentiable curve between the vertices. This curve passed through all vertices, and its radial derivative agrees with the "derivative" of the polygonal line at the vertices. If the clamp shape is given by the sequence of spokes $r(\theta_j)$,i=1 to n, where $\theta_{i+1}=\theta_i+6°$, then the "derivative" at the ith vertex equals $$\frac{r(\theta_{i+1}) - r(\theta_{i-1})}{12}, \text{ when } 2 \leq i \leq n-1, \frac{r(\theta_n) - r(\theta_{n-1})}{6},$$

$$\text{when } i = n, \text{ and } \frac{r(\theta_2) - r(\theta_i)}{6}, \text{ when } i = 1.$$

Also, the curve was computed in such a way that its radial derivative had no zero crossing unless necessary to match the positions and derivatives of the vertices.

5.7 Further Refinements

Further new improvements were made to the prior art Halifax clamp by the present invention, these improvements concerning the interface between the halves of the clamps. This interface is a source of instability in the prior art clamp and can cause the prior art clamp to become loose and dysfunctional. In the prior art clamp, the screw 3 passes through a gliding or sliding hole (which is wider that the outer diameter of screw 3) in the upper C-shaped part 1. The screw 3 attaches to the lower C-shaped part 2 by a threaded hole in the lower part 2. Therefore, in the prior art, no matter how firmly the screw 3 is held by the threaded lower part 2, the upper (gliding) part 1 remains free to rotate about the screw 3.

The present invention minimizes this rotational instability by adding grooves 5, shown in FIG. 20A, radiating from the hole in the footplate of both the upper and the lower part. By tightly approximating the pattern of the radial grooves in the opposing footplates of the upper and lower parts, the present invention minimizes this rotational instability when the assembled device is screwed together. When the upper and lower parts are screwed close together, the two matching patterns of radial grooves in the upper and lower parts mesh together, preventing the upper and lower parts from rotating in relation to each other. As an alternative to radial grooves, sand-blasted or shot-peened surfaces on the mating surfaces of the opposing footplates of the upper and lower parts may be used for the same purpose.

Furthermore, the present invention adds a sleeve 4, shown in FIG. 20 where necessary to slip over the screw 3 between the upper and lower parts 1 and 2. This sleeve 4 is provided with a height "h" and takes up any necessary gap between the upper and lower parts to further insure a good fit. The end of the sleeve 4 also has a matching radial groove pattern 5, or sand blasted or shot-peened mating surface, as described above, to insure rotational stability of the assembled device. The sleeve may be used if necessary to match the combined height of the interlaminar clamps to the anatomic size of the paired laminae, thereby reducing the inventory of clamps required. FIG. 21 shows the sleeve and parts in an assembled condition.

5.8 Examples of Equivalents

The embodiments illustrated and discussed in this specification are intended only to teach those skilled in the art the best way known by the inventor to make and use the invention. Nothing in the specification should be considered as limiting the scope of the present invention. Changes could be made by those skilled in the art to produce equivalent devices and methods without departing from the present invention. The present invention should only be limited by the following claims and their legal equivalents.

For example, a variety of other techniques could be used for measuring and digitizing the specimens. Also, a variety of other mathematics and algorithms could be used for parameterizing, extracting parts, partitioning into clusters, computing clamp shapes to fit the clusters, and for defining fit. Also, sharp inward bends may be smoothed otherwise than by a computer algorithm; for example, they may be smoothed by hand or graphically. Also, the same Moskovich Method can be applied to all of the laminae of the back to make Moskovich clamps for all the vertebrae. Also, the same method can be applied to any surgical implant or medical prosthesis and the body part to which the device must be attached or placed in contact with, whether bone or soft tissue. Basically, this would require that the first step of collecting specimens involve the collection of specimens of the contacted body part in question, rather than just of vertebrae as discussed hereinabove. Furthermore, certain steps that are described in this specification as being done by computer, may also be done otherwise, for example, manually or graphically.

CHART 1

| C1 Top | |
|---|---|
| X | Y |
| −3.191 | −0.335 |
| −3.417 | −0.726 |
| −3.624 | −1.178 |
| −3.813 | −1.698 |
| −3.943 | −2.276 |
| −3.978 | −2.890 |
| −3.510 | −3.160 |
| −2.487 | −2.762 |
| −1.798 | −2.475 |
| 0.391 | −1.203 |
| 0.994 | −2.233 |
| 1.678 | −2.906 |
| 1.973 | −2.715 |
| 2.493 | −2.769 |
| 2.477 | −2.230 |
| 2.426 | −1.763 |
| 2.361 | −1.363 |
| 2.297 | −1.023 |
| 2.278 | −0.740 |
| 2.214 | −0.471 |
| 2.219 | −0.233 |
| 2.144 | 0.000 |
| 2.099 | 0.221 |
| 2.042 | 0.434 |
| 1.996 | 0.649 |
| 1.903 | 0.847 |
| 1.760 | 1.016 |
| 1.451 | 1.054 |
| 1.178 | 1.060 |
| 1.034 | 1.149 |
| 0.905 | 1.245 |
| 0.834 | 1.445 |
| 0.690 | 1.549 |
| 0.536 | 1.651 |
| 0.377 | 1.773 |
| 0.187 | 1.777 |
| 0.000 | 1.788 |
| −0.181 | 1.721 |
| −0.371 | 1.747 |
| −0.587 | 1.805 |
| −0.797 | 1.790 |
| −0.999 | 1.731 |
| −1.208 | 1.663 |
| −1.465 | 1.627 |
| −1.747 | 1.573 |
| −2.027 | 1.473 |
| −2.333 | 1.347 |
| −2.500 | 1.113 |
| −2.582 | 0.839 |
| −2.669 | 0.567 |
| −2.751 | 0.289 |

CHART 2

| C2 Bottom | |
|---|---|
| X | Y |
| −2.593 | −0.273 |
| −2.337 | −0.497 |
| −2.064 | −0.671 |
| −1.894 | −0.843 |
| −1.832 | −1.057 |
| −1.750 | −1.271 |
| −1.640 | −1.477 |
| −1.463 | −1.625 |
| −1.322 | −1.820 |
| −1.143 | −1.981 |
| −0.943 | −2.118 |

CHART 2-continued

C2 Bottom

| X | Y |
|---|---|
| −0.733 | −2.256 |
| −0.495 | −2.330 |
| −0.249 | −2.372 |
| 0.000 | −2.414 |
| 0.265 | −2.521 |
| 0.549 | −2.581 |
| 0.831 | −2.558 |
| 1.075 | −2.416 |
| 1.280 | −2.217 |
| 1.453 | −2.000 |
| 1.726 | −1.917 |
| 1.966 | −1.770 |
| 2.060 | −1.497 |
| 2.131 | −1.230 |
| 2.157 | −0.961 |
| 2.281 | −0.741 |
| 2.350 | −0.499 |
| 2.357 | −0.248 |
| 2.348 | 0.000 |
| 2.393 | 0.252 |
| 2.575 | 0.547 |
| 2.694 | 0.875 |
| 2.874 | 1.280 |
| 3.013 | 1.740 |
| 3.031 | 2.202 |
| 2.312 | 2.082 |
| 2.198 | 2.442 |
| 1.288 | 1.772 |
| −1.219 | 1.678 |
| −1.891 | 2.101 |
| −2.582 | 2.325 |
| −3.313 | 2.407 |
| −3.281 | 1.894 |
| −3.872 | 1.724 |
| −3.735 | 1.214 |
| −3.389 | 0.720 |
| −3.028 | 0.318 |

CHART 3

C2-7 Top A

| X | Y |
|---|---|
| −2.928 | −0.308 |
| −3.032 | −0.644 |
| −3.118 | −1.013 |
| −3.310 | −1.474 |
| −3.481 | −2.010 |
| −3.646 | −2.649 |
| −3.510 | −3.160 |
| −2.487 | −2.762 |
| −2.343 | −3.224 |
| −2.357 | −4.082 |
| −2.310 | −5.189 |
| −1.901 | −5.851 |
| −1.056 | −4.970 |
| 0.000 | 0.000 |
| 0.000 | 0.000 |
| 0.000 | 0.000 |
| 0.391 | −1.203 |
| 0.994 | −2.233 |
| 1.678 | −2.906 |
| 1.897 | −2.611 |
| 2.419 | −2.687 |
| 2.399 | −2.160 |
| 2.318 | −1.684 |
| 2.202 | −1.271 |
| 2.057 | −0.916 |
| 1.936 | −0.629 |
| 1.860 | −0.395 |
| 1.777 | −0.187 |
| 1.730 | 0.000 |

CHART 3-continued

C2-7 Top A

| X | Y |
|---|---|
| 1.704 | 0.179 |
| 1.679 | 0.357 |
| 1.647 | 0.535 |
| 1.639 | 0.730 |
| 1.627 | 0.939 |
| 1.615 | 1.173 |
| 1.587 | 1.429 |
| 1.552 | 1.724 |
| 1.473 | 2.028 |
| 1.350 | 2.339 |
| 1.192 | 2.677 |
| 1.009 | 3.104 |
| 0.776 | 3.651 |
| 0.394 | 3.752 |
| 0.000 | 3.770 |
| −0.369 | 3.510 |
| −0.682 | 3.211 |
| −0.888 | 2.734 |
| −1.100 | 2.471 |
| −1.352 | 2.343 |
| −1.590 | 2.188 |
| −1.810 | 2.010 |
| −2.010 | 1.810 |
| −2.188 | 1.590 |
| −2.333 | 1.347 |
| −2.500 | 1.113 |
| −2.582 | 0.839 |
| −2.669 | 0.567 |
| −2.751 | 0.289 |

CHART 4

C2-7 Top B

| X | Y |
|---|---|
| −3.191 | −0.335 |
| −3.417 | −0.726 |
| −3.624 | −1.178 |
| −3.813 | −1.698 |
| −3.943 | −2.276 |
| −3.978 | −2.890 |
| −3.293 | −2.965 |
| −3.726 | −4.138 |
| −3.675 | −5.058 |
| −3.009 | −5.212 |
| −2.748 | −6.172 |
| −2.276 | −7.004 |
| −1.360 | −6.397 |
| −0.403 | −3.832 |
| 0.000 | 0.000 |
| 0.000 | 0.000 |
| 1.398 | −2.421 |
| 1.973 | −2.715 |
| 2.493 | −2.769 |
| 2.477 | −2.230 |
| 2.426 | −1.763 |
| 2.361 | −1.363 |
| 2.610 | −1.162 |
| 3.234 | −1.051 |
| 3.132 | −0.666 |
| 2.946 | −0.310 |
| 2.816 | 0.000 |
| 2.663 | 0.280 |
| 2.498 | 0.531 |
| 2.363 | 0.768 |
| 2.336 | 1.040 |
| 2.306 | 1.331 |
| 2.214 | 1.609 |
| 2.111 | 1.900 |
| 1.957 | 2.174 |
| 1.799 | 2.476 |
| 1.671 | 2.894 |

CHART 4-continued

C2-7 Top B

| X | Y |
| --- | --- |
| 1.478 | 3.319 |
| 1.169 | 3.598 |
| 0.883 | 4.154 |
| 0.488 | 4.644 |
| 0.000 | 4.541 |
| −0.435 | 4.138 |
| −0.812 | 3.819 |
| −1.014 | 3.121 |
| −1.246 | 2.799 |
| −1.353 | 2.344 |
| −1.470 | 2.023 |
| −1.673 | 1.858 |
| −1.858 | 1.673 |
| −2.023 | 1.470 |
| −2.165 | 1.250 |
| −2.284 | 1.017 |
| −2.271 | 0.738 |
| −2.495 | 0.530 |
| −2.718 | 0.286 |

CHART 5

C3-5 Bottom

| X | Y |
| --- | --- |
| −1.678 | −0.176 |
| −1.602 | −0.340 |
| −1.525 | −0.496 |
| −1.461 | −0.650 |
| −1.393 | −0.804 |
| −1.340 | −0.974 |
| −1.269 | −1.143 |
| −1.159 | −1.287 |
| −1.039 | −1.430 |
| −0.889 | −1.539 |
| −0.732 | −1.645 |
| −0.587 | −1.806 |
| −0.409 | −1.923 |
| −0.222 | −2.115 |
| 0.000 | −2.202 |
| 0.222 | −2.111 |
| 0.449 | −2.111 |
| 0.676 | −2.079 |
| 0.888 | −1.994 |
| 1.039 | −1.800 |
| 1.176 | −1.619 |
| 1.304 | −1.448 |
| 1.407 | −1.267 |
| 1.483 | −1.077 |
| 1.551 | −0.895 |
| 1.554 | −0.692 |
| 1.564 | −0.508 |
| 1.554 | −0.330 |
| 1.537 | −0.162 |
| 1.542 | 0.000 |
| 1.509 | 0.159 |
| 1.470 | 0.312 |
| 1.498 | 0.487 |
| 1.584 | 0.705 |
| 1.642 | 0.948 |
| 1.662 | 1.208 |
| 1.584 | 1.426 |
| 1.596 | 1.773 |
| 1.423 | 1.958 |
| 0.585 | 1.013 |
| 0.589 | 1.322 |
| −0.044 | 0.416 |
| −0.053 | 0.247 |
| −0.173 | 0.532 |
| −0.329 | 0.738 |
| −0.736 | 1.275 |
| −0.717 | 0.987 |

CHART 5-continued

C3-5 Bottom

| X | Y |
| --- | --- |
| −1.038 | 1.153 |
| −2.142 | 1.928 |
| −2.139 | 1.554 |
| −2.058 | 1.188 |
| −1.996 | 0.889 |
| −1.909 | 0.620 |
| −1.839 | 0.391 |
| −1.796 | 0.189 |

CHART 6

C6-7 Bottom

| X | Y |
| --- | --- |
| −2.182 | −0.229 |
| −2.101 | −0.447 |
| −2.009 | −0.653 |
| −1.894 | −0.843 |
| −1.788 | −1.033 |
| −1.684 | −1.223 |
| −1.626 | −1.464 |
| −1.567 | −1.740 |
| −1.474 | −2.029 |
| −1.315 | −2.278 |
| −1.071 | −2.406 |
| −0.849 | −2.613 |
| −0.584 | −2.748 |
| −0.302 | −2.875 |
| 0.000 | −2.844 |
| 0.284 | −2.703 |
| 0.539 | −2.535 |
| 0.821 | −2.526 |
| 1.063 | −2.388 |
| 1.249 | −2.163 |
| 1.422 | −1.957 |
| 1.582 | −1.757 |
| 1.659 | −1.494 |
| 1.704 | −1.238 |
| 1.724 | −0.995 |
| 1.727 | −0.769 |
| 1.767 | −0.574 |
| 1.817 | −0.386 |
| 1.962 | −0.206 |
| 2.108 | 0.000 |
| 2.307 | 0.242 |
| 2.483 | 0.528 |
| 2.736 | 0.889 |
| 2.934 | 1.306 |
| 3.152 | 1.820 |
| 3.171 | 2.304 |
| 2.218 | 1.997 |
| 2.117 | 2.351 |
| 1.690 | 2.327 |
| 1.046 | 1.812 |
| 0.721 | 1.619 |
| 0.352 | 1.084 |
| −0.963 | 2.163 |
| −1.113 | 1.928 |
| −1.356 | 1.866 |
| −2.252 | 2.502 |
| −2.597 | 2.338 |
| −2.993 | 2.174 |
| −2.919 | 1.685 |
| −2.751 | 1.225 |
| −2.613 | 0.849 |
| −2.461 | 0.523 |
| −2.382 | 0.250 |

I claim:

1. An interlaminar clamp comprising:
    an upper portion with an interior surface having a shape a lower portion with an interior surface having a shape, and a screw, between the upper portion and the lower portion, holding the upper and lower portions together, the improvement comprising:

(a) the shape of the interior surface of the upper portion of the clamp following a shape of a curve defined by points indicated by X and Y Cartesian coordinates, as follows:

| C1 Top | |
| --- | --- |
| X | Y |
| −3.191 | −0.335 |
| −3.417 | −0.726 |
| −3.624 | −1.178 |
| −3.813 | −1.698 |
| −3.943 | −2.276 |
| −3.978 | −2.890 |
| −3.510 | −3.160 |
| −2.487 | −2.762 |
| −1.798 | −2.475 |
| 0.391 | −1.203 |
| 0.994 | −2.233 |
| 1.678 | −2.906 |
| 1.973 | −2.715 |
| 2.493 | −2.769 |
| 2.477 | −2.230 |
| 2.426 | −1.763 |
| 2.361 | −1.363 |
| 2.297 | −1.023 |
| 2.278 | −0.740 |
| 2.214 | −0.471 |
| 2.219 | −0.233 |
| 2.144 | 0.000 |
| 2.099 | 0.221 |
| 2.042 | 0.434 |
| 1.996 | 0.649 |
| 1.903 | 0.847 |
| 1.760 | 1.016 |
| 1.451 | 1.054 |
| 1.178 | 1.060 |
| 1.034 | 1.149 |
| 0.905 | 1.245 |
| 0.834 | 1.445 |
| 0.690 | 1.549 |
| 0.536 | 1.651 |
| 0.377 | 1.773 |
| 0.187 | 1.777 |
| 0.000 | 1.788 |
| −0.181 | 1.721 |
| −0.371 | 1.747 |
| −0.587 | 1.805 |
| −0.797 | 1.790 |
| −0.999 | 1.731 |
| −1.208 | 1.663 |
| −1.465 | 1.627 |
| −1.747 | 1.573 |
| −2.027 | 1.473 |
| −2.333 | 1.347 |
| −2.500 | 1.113 |
| −2.582 | 0.839 |
| −2.669 | 0.567 |
| −2.751 | 0.289 | and (b) the shape of the interior surface of the lower portion of the clamp following a shape of a curve defined by points indicated by X and Y Cartesian coordinates as follows:

| C2 Bottom | |
| --- | --- |
| X | Y |
| −2.593 | −0.273 |
| −2.337 | −0.497 |
| −2.064 | −0.671 |
| −1.894 | −0.843 |
| −1.832 | −1.057 |
| −1.750 | −1.271 |
| −1.640 | −1.477 |
| −1.463 | −1.625 |
| −1.322 | −1.820 |
| −1.143 | −1.981 |
| −0.943 | −2.118 |
| −0.733 | −2.256 |
| −0.495 | −2.330 |
| −0.249 | −2.372 |
| 0.000 | −2.414 |
| 0.265 | −2.521 |
| 0.549 | −2.581 |
| 0.831 | −2.558 |
| 1.075 | −2.416 |
| 1.280 | −2.217 |
| 1.453 | −2.000 |
| 1.726 | −1.917 |
| 1.966 | −1.770 |
| 2.060 | −1.497 |
| 2.131 | −1.230 |
| 2.157 | −0.961 |
| 2.281 | −0.741 |
| 2.350 | −0.499 |
| 2.357 | −0.248 |
| 2.348 | 0.000 |
| 2.393 | 0.252 |
| 2.575 | 0.547 |
| 2.694 | 0.875 |
| 2.874 | 1.280 |
| 3.013 | 1.740 |
| 3.031 | 2.202 |
| 2.312 | 2.082 |
| 2.198 | 2.442 |
| 1.288 | 1.772 |
| −1.219 | 1.678 |
| −1.891 | 2.101 |
| −2.582 | 2.325 |
| −3.313 | 2.407 |
| −3.281 | 1.894 |
| −3.872 | 1.724 |
| −3.735 | 1.214 |
| −3.389 | 0.720 |
| −3.028 | 0.318 |

2. The invention in claim 1, wherein the upper and lower portions are formed of a material allowing them to be smoothed to eliminate any sharp inward bends.

3. The invention in claim 1 and further comprising a sleeve sliding over the screw and disposed between the upper portion and the lower portion.

4. The invention in claim 3, wherein the sleeve has two ends, each end having any one of:
   (i) a pattern of grooves radiating from a screw hole in the sleeve,
   (ii) a ball-peened surface, and
   (iii) a sand-blasted surface.

5. The invention in claim 1, wherein each of the upper and lower portions further includes a footplate portion with a surface having any of:
   (i) a pattern of grooves radiating from a screw hole in the footplate portion,
   (ii) a ball-peened surface, and
   (iii) a sand-blasted surface.

6. An interlaminar clamp comprising:
   an upper portion with an interior surface having a shaped a lower portion with an interior surface having a shape, and a screw, between the upper and lower portions, holding the upper and lower portions together, the improvement comprising:

(a) the shape of the interior surface of the upper portion of the clamp following a shape of one curve selected from the group of (i) a curve defined by points indicated by X and Y Cartesian coordinates, as follows:

| C2-7 Top A | |
|---|---|
| X | Y |
| −2.928 | −0.308 |
| −3.032 | −0.644 |
| −3.118 | −1.013 |
| −3.310 | −1.474 |
| −3.481 | −2.010 |
| −3.646 | −2.649 |
| −3.510 | −3.160 |
| −2.487 | −2.762 |
| −2.343 | −3.224 |
| −2.357 | −4.082 |
| −2.310 | −5.189 |
| −1.901 | −5.851 |
| −1.056 | −4.970 |
| 0.000 | 0.000 |
| 0.000 | 0.000 |
| 0.000 | 0.000 |
| 0.391 | −1.203 |
| 0.994 | −2.233 |
| 1.678 | −2.906 |
| 1.897 | −2.611 |
| 2.419 | −2.687 |
| 2.399 | −2.160 |
| 2.318 | −1.684 |
| 2.202 | −1.271 |
| 2.057 | −0.916 |
| 1.936 | −0.629 |
| 1.860 | −0.395 |
| 1.777 | −0.187 |
| 1.730 | 0.000 |
| 1.704 | 0.179 |
| 1.679 | 0.357 |
| 1.647 | 0.535 |
| 1.639 | 0.730 |
| 1.627 | 0.939 |
| 1.615 | 1.173 |
| 1.587 | 1.429 |
| 1.552 | 1.724 |
| 1.473 | 2.028 |
| 1.350 | 2.339 |
| 1.192 | 2.677 |
| 1.009 | 3.104 |
| 0.776 | 3.651 |
| 0.394 | 3.752 |
| 0.000 | 3.770 |
| −0.369 | 3.510 |
| −0.682 | 3.211 |
| −0.888 | 2.734 |
| −1.100 | 2.471 |
| −1.352 | 2.343 |
| −1.590 | 2.188 |
| −1.810 | 2.010 |
| −2.010 | 1.810 |
| −2.188 | 1.590 |
| −2.333 | 1.347 |
| −2.500 | 1.113 |
| −2.582 | 0.839 |
| −2.669 | 0.567 |
| −2.751 | 0.289 | and (ii) a curve defined by points indicated by X and Y Cartesian coordinates, as follows:

| C2-7 Top B | |
|---|---|
| X | Y |
| −3.191 | −0.335 |
| −3.417 | −0.726 |
| −3.624 | −1.178 |
| −3.813 | −1.698 |
| −3.943 | −2.276 |
| −3.978 | −2.890 |
| −3.293 | −2.965 |
| −3.726 | −4.138 |
| −3.675 | −5.058 |
| −3.009 | −5.212 |
| −2.748 | −6.172 |
| −2.276 | −7.004 |
| −1.360 | −6.397 |
| −0.403 | −3.832 |
| 0.000 | 0.000 |
| 0.000 | 0.000 |
| 1.398 | −2.421 |
| 1.973 | −2.715 |
| 2.493 | −2.769 |
| 2.477 | −2.230 |
| 2.426 | −1.763 |
| 2.361 | −1.363 |
| 2.610 | −1.162 |
| 3.234 | −1.051 |
| 3.132 | −0.666 |
| 2.946 | −0.310 |
| 2.816 | 0.000 |
| 2.663 | 0.280 |
| 2.498 | 0.531 |
| 2.363 | 0.768 |
| 2.336 | 1.040 |
| 2.306 | 1.331 |
| 2.214 | 1.609 |
| 2.111 | 1.900 |
| 1.957 | 2.174 |
| 1.799 | 2.476 |
| 1.671 | 2.894 |
| 1.478 | 3.319 |
| 1.169 | 3.598 |
| 0.883 | 4.154 |
| 0.488 | 4.644 |
| 0.000 | 4.541 |
| −0.435 | 4.138 |
| −0.812 | 3.819 |
| −1.014 | 3.121 |
| −1.246 | 2.799 |
| −1.353 | 2.344 |
| −1.470 | 2.023 |
| −1.673 | 1.858 |
| −1.858 | 1.673 |
| −2.023 | 1.470 |
| −2.165 | 1.250 |
| −2.284 | 1.017 |
| −2.271 | 0.738 |
| −2.495 | 0.530 |
| −2.718 | 0.286 | and (b) the shape of the interior surface of the lower portion of the clamp following a shape of one curve selected from the group of (i) a curve defined by points indicated by X and Y Cartesian coordinates, as follows:

| C3-5 Bottom | |
|---|---|
| X | Y |
| −1.678 | −0.176 |
| −1.602 | −0.340 |
| −1.525 | −0.496 |
| −1.461 | −0.650 |
| −1.393 | −0.804 |
| −1.340 | −0.974 |

C3-5 Bottom

| X | Y |
|---|---|
| -1.269 | -1.143 |
| -1.159 | -1.287 |
| -1.039 | -1.430 |
| -0.889 | -1.539 |
| -0.732 | -1.645 |
| -0.587 | -1.806 |
| -0.409 | -1.923 |
| -0.222 | -2.115 |
| 0.000 | -2.202 |
| 0.222 | -2.111 |
| 0.449 | -2.111 |
| 0.676 | -2.079 |
| 0.888 | -1.994 |
| 1.039 | -1.800 |
| 1.176 | -1.619 |
| 1.304 | -1.448 |
| 1.407 | -1.267 |
| 1.483 | -1.077 |
| 1.551 | -0.895 |
| 1.554 | -0.692 |
| 1.564 | -0.508 |
| 1.554 | -0.330 |
| 1.537 | -0.162 |
| 1.542 | 0.000 |
| 1.509 | 0.159 |
| 1.470 | 0.312 |
| 1.498 | 0.487 |
| 1.584 | 0.705 |
| 1.642 | 0.948 |
| 1.662 | 1.208 |
| 1.584 | 1.426 |
| 1.596 | 1.773 |
| 1.423 | 1.958 |
| 0.585 | 1.013 |
| 0.589 | 1.322 |
| -0.044 | 0.416 |
| -0.053 | 0.247 |
| -0.173 | 0.532 |
| -0.329 | 0.738 |
| -0.736 | 1.275 |
| -0.717 | 0.987 |
| -1.038 | 1.153 |
| -2.142 | 1.928 |
| -2.139 | 1.554 |
| -2.058 | 1.188 |
| -1.996 | 0.889 |
| -1.909 | 0.620 |
| -1.839 | 0.391 |
| -1.796 | 0.189 | and (ii) a curve defined by points indicated by X and Y Cartesian coordinates, as follows:

C6-7 Bottom

| X | Y |
|---|---|
| -2.182 | -0.229 |
| -2.101 | -0.447 |
| -2.009 | -0.653 |
| -1.894 | -0.843 |
| -1.788 | -1.033 |
| -1.684 | -1.223 |
| -1.626 | -1.464 |
| -1.567 | -1.740 |
| -1.474 | -2.029 |
| -1.315 | -2.278 |
| -1.071 | -2.406 |
| -0.849 | -2.613 |
| -0.584 | -2.748 |
| -0.302 | -2.875 |
| 0.000 | -2.844 |
| 0.284 | -2.703 |
| 0.539 | -2.535 |
| 0.821 | -2.526 |
| 1.063 | -2.388 |
| 1.249 | -2.163 |
| 1.422 | -1.957 |
| 1.582 | -1.757 |
| 1.659 | -1.494 |
| 1.704 | -1.238 |
| 1.724 | -0.995 |
| 1.727 | -0.769 |
| 1.767 | -0.574 |
| 1.817 | -0.386 |
| 1.962 | -0.206 |
| 2.108 | 0.000 |
| 2.307 | 0.242 |
| 2.483 | 0.528 |
| 2.736 | 0.889 |
| 2.934 | 1.306 |
| 3.152 | 1.820 |
| 3.171 | 2.304 |
| 2.218 | 1.997 |
| 2.117 | 2.351 |
| 1.690 | 2.327 |
| 1.046 | 1.812 |
| 0.721 | 1.619 |
| 0.352 | 1.084 |
| -0.963 | 2.163 |
| -1.113 | 1.928 |
| -1.356 | 1.866 |
| -2.252 | 2.502 |
| -2.597 | 2.338 |
| -2.993 | 2.174 |
| -2.919 | 1.685 |
| -2.751 | 1.225 |
| -2.613 | 0.849 |
| -2.461 | 0.523 |
| -2.382 | 0.250 |

7. The invention in claim 6, wherein the upper and lower portions are formed of a material allowing them to be smoothed to eliminate any sharp inward bends.

8. The invention in claim 6 and further comprising a sleeve sliding over the screw and disposed between the upper portion and the lower portion.

9. The invention in claim 8, wherein the sleeve has two ends, each end having any one of:
   (i) a pattern of grooves radiating from a screw hole in the sleeve,
   (ii) a ball-peened surface, and
   (iii) a sand-blasted surface.

10. The invention in claim 6, wherein each of the upper and lower portions further includes a footplate portion with a surface having any of:
    (i) a pattern of grooves radiating from a screw hole in the footplate portion,
    (ii) a ball-peened surface, and
    (iii) a sand-blasted surface.

* * * * *